US012709645B2

(12) United States Patent
Rogers

(10) Patent No.: US 12,709,645 B2

(45) Date of Patent: Aug. 18, 2026

(54) TARGETING GENE AMPLIFICATION IN CANCER USING TRIPLEX FORMATION AS A THERAPEUTIC STRATEGY

(71) Applicant: Yale University, New Haven, CT (US)

(72) Inventor: Faye A. Rogers, Norwalk, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 17/850,793

(22) Filed: Jun. 27, 2022

(65) Prior Publication Data

US 2023/0027885 A1 Jan. 26, 2023

Related U.S. Application Data

(63) Continuation of application No. 16/683,205, filed on Nov. 13, 2019, now Pat. No. 11,401,340.

(60) Provisional application No. 62/767,279, filed on Nov. 14, 2018.

(51) Int. Cl.

| | |
|---|---|
| ***C07H 21/04*** | (2006.01) |
| ***A61K 47/54*** | (2017.01) |
| ***A61K 47/68*** | (2017.01) |
| ***C07K 16/30*** | (2006.01) |
| ***C12N 15/113*** | (2010.01) |

(52) U.S. Cl.

CPC ........ *C07K 16/3015* (2013.01); *A61K 47/543* (2017.08); *A61K 47/6807* (2017.08); *C12N 15/113* (2013.01); *C07K 2317/73* (2013.01); *C07K 2317/76* (2013.01); *C12N 2310/15* (2013.01)

(58) Field of Classification Search

CPC .......................... C12N 15/113; C12N 2310/15

See application file for complete search history.

(56) References Cited

U.S. PATENT DOCUMENTS

| | | | | |
|---|---|---|---|---|
| 7,279,463 | B2 | 10/2007 | Glazer | |
| 9,587,238 | B1 | 3/2017 | Rogers | |
| 11,401,340 | B2 | 8/2022 | Rogers | |
| 2011/0293585 | A1* | 12/2011 | del Campo .......... | C12N 15/113 536/23.1 |
| 2014/0364460 | A1 | 12/2014 | Freed-Pastor et al. | |
| 2021/0222175 | A1 | 7/2021 | Rogers | |

FOREIGN PATENT DOCUMENTS

| | | | | |
|---|---|---|---|---|
| WO | WO-9415616 A1 * | 7/1994 | ......... | C12N 15/1138 |
| WO | 2014/078749 A1 | 5/2014 | | |

OTHER PUBLICATIONS

Li et al. (Frontiers in Pharmacology, 2022, 13, 1-9).*
Ebbinghaus et al. (J Clin Invest, 1993, 92(5), 2433-9).*
Seliger et al. (Int. J. Cancer, 87, 349-359, 2000).*
Faria et al. (The Journal of Gene Medicine, 2001, 3, 299-310).*
Cheng et al. (The Journal of Pharmacology and Experimental Therapeutics, 317, 2, 797-805, 2006).*
Vasquez et al. (The Journal of Biological Chemistry, 276, 42, 38536-38541, 2001).*
Guntaka et al. (The International Journal of Biochemistry & Cell Biology 35 (2003) 22-31).*
U.S. Appl. No. 17/160,050, filed Jan. 27, 2021, Rogers.
[No Author Listed], TFOs Directly Targeting Amplified Oncogenic Drivers Promote Apoptosis. Cancer Discov. Nov. 5, 2021. doi: 10.1158/2159-8290.CD-RW2021-161. Epub ahead of print.
Akouchekian et al., Does PTEN gene mutation play any role in Li-Fraumeni syndrome. Med J Islam Repub Iran. May 29, 2016;30:378.
Aladjem et al., ES cells do not activate p53-dependent stress responses and undergo p53-independent apoptosis in response to DNA damage. Curr Biol. Jan. 29, 1998;8(3):145-55.
Brodowicz et al., Anti-Her-2/neu antibody induces apoptosis in Her-2/neu overexpressing breast cancer cells independently from p53 status. Br J Cancer. Nov. 30, 2001;85(11):1764-70.
Dart, Amplifying targeting. Nat Rev Cancer. Jan. 2022;22(1):3. doi: 10.1038/s41568-021-00429-y.
Fowler, Potential New Therapeutic Option May Combat Drug Resistance in HER2+ Breast Cancer and Ovarian Cancer. Cancer Network. Dec. 3, 2021. https://www.cancernetwork.com/view/potential-new-therapeutic-option-may-combat-drug-resistance-in-her2-breast-cancer-and-ovarian-cancer [last accessed Jan. 6, 2022]. 2 pages.
Kaushik et al., XPD-dependent activation of apoptosis in response to triplex-induced DNA damage. Nucleic Acids Res. Oct. 2013;41(19):8979-94. doi: 10.1093/nar/gkt670. Epub Aug. 2, 2013.
Knauert et al., Triplex forming oligonucleotides: sequence-specific tools for gene targeting. Hum Mol Genet. Oct. 1, 2001;10(20):2243-51.
Liu et al., Normal cells, but not cancer cells, survive severe Plk1 depletion. Mol Cell Biol. Mar. 2006;26(6):2093-108.
Mehta et al., Negative regulation of chemokine receptor CXCR4 by tumor suppressor p53 in breast cancer cells: implications of p53 mutation or isoform expression on breast cancer cell invasion. Oncogene. May 17, 2007;26(23):3329-37.
Montazeri et al., P53 but not cyclin E acts in a negative regulatory loop to control HER-2 expression in MCF-7 breast carcinoma cell line. Acta Med Iran. Sep. 9, 2013;51(8):513-9.
Nichols et al., Germ-line p53 mutations predispose to a wide spectrum of early-onset cancers. Cancer Epidemiol Biomarkers Prev. Feb. 2001;10(2):83-7.
Porumb et al., Temporary ex vivo inhibition of the expression of the human oncogene HER2 (NEU) by a triple helix-forming oligonucleotide. Cancer Res. Feb. 1, 1996;56(3):515-22.
Rivlin et al., Mutations in the p53 Tumor Suppressor Gene: Important Milestones at the Various Steps of Tumorigenesis. Genes Cancer. Apr. 2011;2(4):466-74. doi: 10.1177/1947601911408889.

(Continued)

*Primary Examiner* — Amy Rose Hudson

(57) ABSTRACT

Disclosed herein are methods and agents for the treatment of cancer using p53-independent apoptosis to reduce the number of p53-depleted or p53-mutated cancer cells that have amplified HER2 gene. Also disclosed herein are methods and agents for the treatment of HER2-positive cancer in individuals with Li-Fraumeni Syndrome.

9 Claims, 18 Drawing Sheets

Specification includes a Sequence Listing.

(56) References Cited

OTHER PUBLICATIONS

Rogers et al., Improved bioactivity of G-rich triplex-forming oligonucleotides containing modified guanine bases. Artif DNA PNA XNA. 2014;5(1):e27792. doi: 10.4161/adna.27792.
Rogers, Exploiting Gene Amplification in Cancer Using Triplex Formation as a Novel Therapeutic Strategy. ASGCT Abstract. 2018. 1 page.
Rogers, Exploiting Gene Amplification in Cancer Using Triplex Formation as a Novel Therapeutic Strategy. ASGCT Poster. 2018. 1 page.
Smith et al., p53 regulation of DNA excision repair pathways. Mutagenesis. Mar. 2002;17(2):149-56.
Tanida et al., Mechanisms of Cisplatin-Induced Apoptosis and of Cisplatin Sensitivity: Potential of BIN1 to Act as a Potent Predictor of Cisplatin Sensitivity in Gastric Cancer Treatment. Int J Surg Oncol. 2012;2012:862879. doi: 10.1155/2012/862879. Epub Jun. 12, 2012.
Tiwari et al., Direct targeting of amplified gene loci for proapoptotic anticancer therapy. Nat Biotechnol. Oct. 28, 2021. doi: 10.1038/s41587-021-01057-5. Epub ahead of print.
Tiwari et al., Triplex structures induce DNA double strand breaks via replication fork collapse in NER deficient cells. Nucleic Acids Res. Sep. 19, 2016;44(16):7742-54. doi: 10.1093/nar/gkw515. Epub Jun. 13, 2016.
Wang et al., The XPB and XPD DNA helicases are components of the p53-mediated apoptosis pathway. Genes Dev. May 15, 1996;10(10):1219-32.
Zhou et al., Recognition of RNA duplexes by chemically modified triplex-forming oligonucleotides. Nucleic Acids Res. Jul. 2013;41(13):6664-73. doi: 10.1093/nar/gkt352. Epub May 8, 2013.
Zhu et al., Lipid and polymeric carrier-mediated nucleic acid delivery. Expert Opin Drug Deliv. Oct. 2010;7(10):1209-26.
Benfield et al., Targeted generation of DNA strand breaks using pyrene-conjugated triplex-forming oligonucleotides. Biochemistry. Jun. 10, 2008;47(23):6279-88. doi: 10.1021/bi7024029. Epub May 13, 2008.
Sedelnikova et al., Sequence-specific gene cleavage in intact mammalian cells by $^{125}$I-labeled triplex-forming oligonucleotides conjugated with nuclear localization signal peptide. Antisense Nucleic Acid Drug Dev. Feb. 2002;12(1):43-9. doi: 10.1089/108729002753670256.
Yabuki et al., Gene amplification and expression in lung cancer cells with acquired paclitaxel resistance. Cancer Genet Cytogenet. Feb. 2007;173(1):1-9. doi: 10.1016/j.cancergencyto.2006.07.020.

* cited by examiner

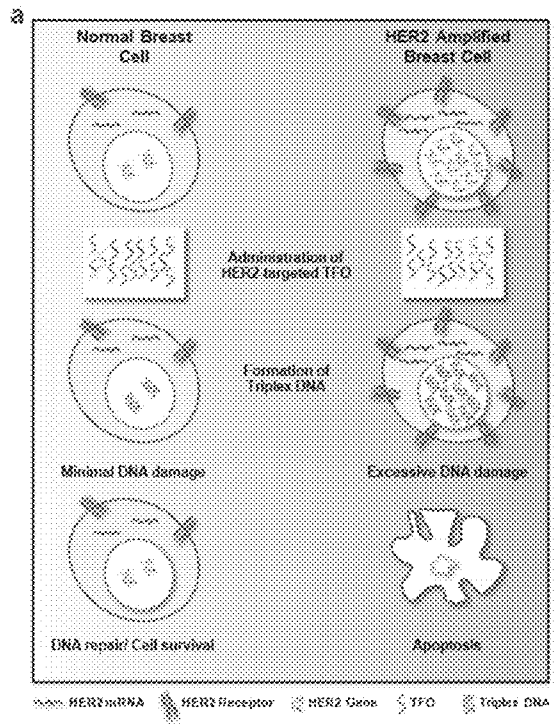
FIG. 1A
| HER2 Gene Amplification in Breast Cancer Cell Lines | |
|---|---|
| Cell Line | HER2 Copy Number |
| BT20 | null |
| MCF7 | 2 |
| MDA-MB-453 | 11 |
| SKBR3 | 31 |
| BT474 | 52 |
FIG. 1B
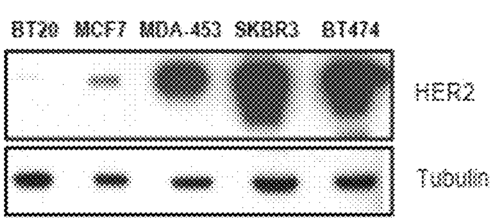
FIG. 1C

SEQUENCE LISTING

```
<160> NUMBER OF SEQ ID NOS: 13

<210> SEQ ID NO 1
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1

aggagaagga ggaggtggag gaggaggg                                   28


<210> SEQ ID NO 2
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 2
```

-continued gggggcaag agggcgagga ggagcccc 28

<210> SEQ ID NO 3
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 3
gggaggagga ggtggaggag gaagagga 28

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4
gaggaggagt gggagaatgg gggg 24

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 5
ggggtgagga gagtggggga ggagaaaggg 30

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
ggggtgggag ggacaaaggg gg 22

<210> SEQ ID NO 7
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 7
gggaaagagg agggggtgag aggagtgggg 30

<210> SEQ ID NO 8
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 8
gggggaaata gggagggtgg gg 22

<210> SEQ ID NO 9
<211> LENGTH: 24
<212> TYPE: DNA

-continued

```
<213> ORGANISM: Artificial Sequence
<220> FEATURE:
<223> OTHER INFORMATION: Synthetic Polynucleotide

<400> SEQUENCE: 9

agtcagtcag tcagtcagtc agtc                                              24


<210> SEQ ID NO 10
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 10

ccctcctcct ccacctcctc cttctcct                                          28


<210> SEQ ID NO 11
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 11

ggggctcctc ctcgccctct tgcccccc                                          28


<210> SEQ ID NO 12
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 12

ccctttctcc tcccccactc tcctcacccc                                        30


<210> SEQ ID NO 13
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 13

ccccctttgt ccctcccacc cc                                                22
```

TARGETING GENE AMPLIFICATION IN CANCER USING TRIPLEX FORMATION AS A THERAPEUTIC STRATEGY

RELATED APPLICATIONS

This application is a continuation application of U.S. application Ser. No. 16/683,205, filed Nov. 13, 2019, which claims the benefit under 35 U.S.C. § 119 (e) of U.S. provisional application Ser. No. 62/767,279, filed Nov. 14, 2018. The teachings and text of the aforementioned applications are incorporated by reference herein in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 27, 2022, is named Y008770146US03-SEQ-JXV and is 2,940 bytes in size.

GOVERNMENT SUPPORT

This invention was made with government support under R21CA185192 and R01GM126211 awarded by the National Institutes of Health. The government has certain rights in the invention.

BACKGROUND

Gene amplification often leads to higher expression of genes involved in normal cell growth and survival pathways[1,2]. As such, gene amplification is a major mechanism driving oncogenesis in a broad spectrum of cancers, ultimately affecting tumor progression and clinical outcome[3,4]. Several drugs have been developed to inhibit the oncogenic activity of amplified driver genes[5]. The majority of these cancer therapeutics target the overexpressed protein products and their clinical efficacy is often hampered by drug resistance[6,7].

SUMMARY

Described herein is a novel therapeutic method for the treatment of cancers that are characterized by gene amplification, and, in one embodiment specifically, the treatment of cancers that are characterized by HER2 gene amplification. In the method, manipulation of the DNA damage response with triplex-forming oligonucleotides (TFOs) drives p53-independent tumor-specific induction of apoptosis. The method described is particularly applicable to p53-independent cancers, which are often aggressive and resistant to traditional chemotherapeutic drugs. This provides a new and specific approach in targeted cancer therapy, which can have enormous impact on the field of precision medicine.

Accordingly, one aspect of the present disclosure provides a method of reducing, in a population of cells, the number of p53-depleted cancer cells in which a HER2 gene is amplified, the method comprising contacting p53-depleted cancer cells with triplex forming oligonucleotides (TFOs) targeted to a polypurine target site in the amplified-HER2 gene, under conditions under which the TFOs enter the p53-depleted cancer cells in sufficient quantity to induce apoptosis. In some embodiments, the p53-depleted cells are mammalian cells. In some embodiments, the p53-depleted cells are human cells. In some embodiments, the polypurine target site is/comprises SEQ ID NO: 1, SEQ ID NO: 2, SEQ ID NO:5 or SEQ ID NO:6. In some embodiments, the TFOs are at least 13 nucleotides in length. In some embodiments, the TFOs are at least 22 nucleotides in length. In some embodiments, at least 13 of the nucleotides hybridize to SEQ ID NO: 1, SEQ ID NO: 2, SEQ ID NO:5 or SEQ ID NO:6.

TFOs can be administered individually (e.g., all TFOs administered have the same sequence) or a combination of two or more TFOs can be administered (e.g., TFOs administered comprise different nucleotide sequences). In some embodiments, the TFOs comprise a nucleotide sequence at least 90% identical to SEQ ID NO: 3; a nucleotide sequence at least 90% identical to SEQ ID NO: 4; a nucleotide sequence at least 90% identical to SEQ ID NO: 7; a nucleotide at least 90% identical to SEQ ID NO: 8; or a combination of two, three or four of the foregoing. For example, TFOs administered can comprise a nucleotide sequence at least 90% identical to SEQ ID NO: 3 and a nucleotide sequence at least 90% identical to SEQ ID NO: 4; a nucleotide sequence at least 90% identical to SEQ ID NO: 3 and a nucleotide sequence at least 90% identical to SEQ ID NO: 7; a nucleotide sequence at least 90% identical to SEQ ID NO: 3 and a nucleotide at least 90% identical to SEQ ID NO: 8; a nucleotide sequence at least 90% identical to SEQ ID NO: 4 and a nucleotide sequence at least 90% identical to SEQ ID NO: 7; a nucleotide sequence at least 90% identical to SEQ ID NO: 4 and a nucleotide sequence at least 90% identical to SEQ ID NO:8; a nucleotide sequence at least 90% identical to SEQ ID NO: 7 and a nucleotide sequence at least 90% identical to SEQ ID NO: 8.

In some embodiments, three different TFOs are administered. For example, the following can be administered:

- a TFO that comprises a nucleotide sequence at least 90% identical to SEQ ID NO: 3, a TFO that comprises a nucleotide sequence at least 90% identical to SEQ ID NO: 4 and a TFO that comprises a nucleotide sequence at least 90% identical to SEQ ID NO: 7;
- a TFO that comprises a nucleotide sequence at least 90% identical to SEQ ID NO: 3, a TFO that comprises a nucleotide sequence at least 90% identical to SEQ ID NO: 4 and a TFO that comprises a nucleotide sequence, at least 90% identical to SEQ ID NO: 8;
- a TFO that comprises a nucleotide sequence at least 90% identical to SEQ ID NO: 3, a TFO that comprises a nucleotide sequence at least 90% identical to SEQ ID NO: 7 and a TFO that comprises a nucleotide sequence at least 90% identical to SEQ ID NO: 8; or
- a TFO that comprises a nucleotide sequence at least 90% identical to SEQ ID NO: 4, TFO that comprises a nucleotide sequence at least 90% identical to SEQ ID NO: 7 and a TFO that comprises a nucleotide sequence at least 90% identical to SEQ ID NO: 8.

In further embodiments, four different TFOs are administered: a (at least one) TFO that comprises a nucleotide sequence at least 90% identical to SEQ ID NO: 3; a (at least one) TFO that comprises a nucleotide sequence at least 90% identical to SEQ ID NO: 4; a (at least one) TFO that comprises a nucleotide sequence at least 90% identical to SEQ ID NO: 7; and a (at least one) TFO that comprises a nucleotide at least 90% identical to SEQ ID NO: 8.

Alternatively, TFOs that comprise a nucleotide sequence identical to SEQ ID NO: 3; TFOs that comprise a nucleotide sequence identical to SEQ ID NO: 4; TFOs that comprise a nucleotide sequence identical to SEQ ID NO: 7; and TFOs that comprise a nucleotide sequence identical to SEQ ID NO: 8 can be administered individually (e.g., all TFOs administered have the same sequence) or a combination of two or more TFOs can be administered (e.g., TFOs administered comprise different nucleotide sequences).

For example, TFOs administered can comprise a nucleotide sequence identical to SEQ ID NO: 3 and a nucleotide sequence identical to SEQ ID NO: 4; a nucleotide sequence identical to SEQ ID NO: 3 and a nucleotide sequence identical to SEQ ID NO: 7; a nucleotide sequence identical to SEQ ID NO: 3 and a nucleotide sequence identical to SEQ ID NO: 8; a nucleotide sequence identical to SEQ ID NO: 4 and a nucleotide sequence identical to SEQ ID NO: 7; a nucleotide sequence identical to SEQ ID NO: 4 and a nucleotide sequence identical to SEQ ID NO:8; a nucleotide sequence identical to SEQ ID NO: 7 and a nucleotide sequence identical to SEQ ID NO: 8.

In some embodiments, three different TFOs are administered. For example, the following can be administered:

a TFO that comprises a nucleotide sequence identical to SEQ ID NO: 3, a TFO that comprises a nucleotide sequence identical to SEQ ID NO: 4 and a TFO that comprises a nucleotide sequence identical to SEQ ID NO: 7;

a TFO that comprises a nucleotide sequence identical to SEQ ID NO: 3, a TFO that comprises a nucleotide sequence identical to SEQ ID NO: 4 and a TFO that comprises a nucleotide sequence identical to SEQ ID NO: 8;

a TFO that comprises a nucleotide sequence identical to SEQ ID NO: 3, a TFO that comprises a nucleotide sequence identical to SEQ ID NO: 7 and a TFO that comprises a nucleotide sequence identical to SEQ ID NO: 8; or a TFO that comprises a nucleotide sequence identical to SEQ ID NO: 4, a TFO that comprises a nucleotide sequence identical to SEQ ID NO: 7 and a TFO that comprises a nucleotide sequence identical to SEQ ID NO: 8.

In further embodiments, four different TFOs are administered: a (at least one) TFO that comprises a nucleotide sequence identical to SEQ ID NO: 3; a (at least one) TFO that comprises a nucleotide sequence identical to SEQ ID NO: 4; a (at least one) TFO that comprises a nucleotide sequence identical to SEQ ID NO: 7; and a (at least one) TFO that comprises a nucleotide identical to SEQ ID NO: 8.

In some embodiments, the triplex forming oligonucleotides (TFOs) are in a delivery vehicle or are conjugated to a delivery vehicle. In some embodiments, the delivery vehicle is lipid nanoparticles. In some embodiments, the TFOs have backbone modifications. In some embodiments, the backbone modifications include phosphorothioates, phosphorodithioates, methylphosphonates, phosphoramidates, boranophosphate oligos, polyamides, methylene(methylimino) linkages, morpholine oligos, or some combination thereof. In some embodiments, the p53-depleted cancer cells are renal cell carcinoma cells, lung cancer cells, colon cancer cells, colon carcinoma cells, ovarian cancer cells, breast cancer cells, colorectal cancer cells, gastric cancer cells, and/or endometrial cancer cells.

Another aspect of the present disclosure provides a method of reducing, in a population of cells, the number of p53-mutated cancer cells in which a HER2 gene is amplified, the method comprising contacting p53-mutated cancer cells with triplex forming oligonucleotides (TFOs) targeted to a polypurine site in the amplified-HER2 gene, under conditions under which the TFOs enter the p53-mutated cancer cells in sufficient quantity to induce apoptosis. In some embodiments, the p53-mutated cells are mammalian cells. In some embodiments, the p53-mutated cells are human cells. In some embodiments, the polypurine target site is SEQ ID NO: 1, SEQ ID NO: 2, SEQ ID NO:5 or SEQ ID NO:6. In some embodiments, the TFOs are at least 13 nucleotides in length. In some embodiments, the TFOs are at least 22 nucleotides in length. In some embodiments, at least 13 of the nucleotides hybridize to SEQ ID NO: 1, SEQ ID NO: 2, SEQ ID NO:5 or SEQ ID NO:6. In some embodiments, the TFOs comprise a nucleotide sequence at least 90% identical to SEQ ID NO: 3, and/or a nucleotide sequence at least 90% identical to SEQ ID NO: 4, and/or a nucleotide sequence at least 90% identical to SEQ ID NO: 7 and/or a nucleotide at least 90% identical to SEQ ID NO: 8. In some embodiments, the TFOs are in a delivery vehicle or are conjugated to a delivery vehicle. In some embodiments, the delivery vehicle is lipid nanoparticles. In some embodiments, the TFOs have backbone modifications. In some embodiments, the backbone modifications include phosphorothioates, phosphorodithioates, methylphosphonates, phosphoramidates, boranophosphate oligos, polyamides, methylene(methylimino) linkages, morpholino oligos, or some combination thereof. In some embodiments, the p53-mutated cancer cells are renal cell carcinoma cells, lung cancer cells, colon cancer cells, colon carcinoma cells, ovarian cancer cells, breast cancer cells, colorectal cancer cells, gastric cancer cells, and/or endometrial cancer cells.

Another aspect of the present disclosure provides a method of treating cancer in an individual with Li-Fraumeni syndrome, the method comprising administering to the individual TFOs targeted to a polypurine target site in an amplified-HER2 gene, under conditions under which the TFOs enter p53-depleted cancer cells in sufficient quantity to induce apoptosis. In some embodiments, the polypurine target site is SEQ ID NO: 1, SEQ ID NO: 2, SEQ ID NO:5 or SEQ ID NO:6. In some embodiments, the TFOs are at least 13 nucleotides in length. In some embodiments, the TFOs are at least 22 nucleotides in length. In some embodiments, at least 13 of the nucleotides hybridize to SEQ ID NO: 1, SEQ ID NO: 2, SEQ ID NO:5 or SEQ ID NO:6. In some embodiments, the TFOs comprise a nucleotide sequence at least 90% identical to SEQ ID NO: 3, and/or a nucleotide sequence at least 90% identical to SEQ ID NO: 4, and/or a nucleotide sequence at least 90% identical to SEQ ID NO: 7 and/or a nucleotide at least 90% identical to SEQ ID NO: 8. In some embodiments, the TFOs are in a delivery vehicle or are conjugated to a delivery vehicle. In some embodiments, the delivery vehicle is lipid nanoparticles. In some embodiments, the TFOs are encapsulated in the lipid nanoparticles. In some embodiments, the TFOs have backbone modifications. In some embodiments, the backbone modifications include phosphorothioates, phosphorodithioates, methylphosphonates, phosphoramidates, boranophosphate polyamides, methylene (methylimino) linkages, morpholino oligos, or some combination thereof. In some embodiments, the TFOs are administered by injection. In some embodiments, the TFOs are administered intratumorally or intraperitoneally. In some embodiments, an anticancer agent that is not a TFO is administered with the TFOs.

In some embodiments, the anticancer agent is a protein, a nucleic acid, a small molecule, or a drug. In some embodiments, the anticancer agent is a protein, a nucleic acid, a small molecule, or a drug.

Another aspect of the present disclosure provides a method of administering TFOs for the treatment of cancer, the method comprising preparing a mixture of TFOs targeted to a polypurine target site in an amplified-HER2 gene and administering the mixture of TFOs to an individual, in sufficient quantity to induce p53-independent apoptosis. In some embodiments, the mixture of TFOs is encapsulated in lipid nanoparticles. In some embodiments, the polypurine target site is SEQ ID NO: 1, SEQ ID NO: 2, SEQ ID NO:5 or SEQ ID NO:6. In some embodiments, the TFOs are at least 13 nucleotides in length. In some embodiments, the TFOs are at least 22 nucleotides in length. In some embodiments, at least 13 of the nucleotides hybridize to SEQ ID NO: 1, SEQ ID NO: 2, SEQ ID NO:5 or SEQ ID NO:6. In some embodiments, the mixture of TFOs comprises a nucleotide sequence at least 90% identical to SEQ ID NO: 3, and/or a nucleotide sequence at least 90% identical to SEQ ID NO: 4, and/or a nucleotide sequence at least 90% identical to SEQ ID NO: 7 and/or nucleotide at least 90% identical to SEQ ID NO: 8. In some embodiments, the TFOs have backbone modifications. In some embodiments, the backbone modifications include phosphorothioates, phosphorodithioates, methylphosphonates, phosphoramidates, boranophosphate oligos, polyamides, methylene(methylimino) linkages, morpholino oligos, or some combination thereof. In some embodiments, the mixture of TFOs is administered by injection. In some embodiments, the mixture of TFOs is administered intratumorally or intraperitoneally. In some embodiments, an anticancer agent that is not a TFO is administered with the mixture of TFOs. In some embodiments, the anticancer agent is a protein, a nucleic acid, a small molecule, or a drug. In some embodiments, the individual is a mammal. In some embodiments, the individual is a human. In some embodiments, the individual is a model of cancer. In some embodiments, the cancer is a carcinoma, a sarcoma or a melanoma with HER-2 gene amplification. In some embodiments, the model of cancer is selected from a group including a p53-knockout mouse, a Li-Fraumeni Syndrome mouse, a mouse with MDA-MB-453 cells, SKBR3 cells, BT474 cells, PEO1 cells, SKOV3 cells, and p53-knockout mouse.

Another aspect of the present disclosure provides a composition, comprising TFOs targeted to a polypurine target site in an amplified-HER2 gene in sufficient quantity to induce p53-independent apoptosis in a p53-depleted cancer cell or a p53-mutated cancer cell, a pharmaceutically acceptable carrier, and optionally lipid nanoparticles, wherein the TFOs are encapsulated in the lipid nanoparticles or are conjugated to the lipid nanoparticles. In some embodiments, the polypurine target site is SEQ ID NO: 1, SEQ ID NO: 2, SEQ ID NO:5 or SEQ ID NO:6. In some embodiments, the TFOs are at least 13 nucleotides in length. In some embodiments, the TFOs are at least 22 nucleotides in length. In some embodiments, at least 13 of the nucleotides hybridize to SEQ ID NO: 1, SEQ ID NO: 2, SEQ ID NO:5 or SEQ ID NO:6. In some embodiments, the TFOs comprise a nucleotide sequence at least 90% identical to SEQ ID NO: 3, and/or a nucleotide sequence at least 90% identical to SEQ ID NO: 4, and/or a nucleotide sequence at least 90% identical to SEQ ID NO: 7 and/or a nucleotide at least 90% identical to SEQ ID NO: 8. In some embodiments, the TFOs have backbone modifications. In some embodiments, the backbone modifications include phosphorothioates, phosphorodithioates, methylphosphonates, phosphoramidates, boranophosphate oligos, polyamides, methylene(methylimino) linkages, morpholino oligos, or some combination thereof. In some embodiments, the pharmaceutically acceptable carrier comprises water or saline.

The details of one or more embodiments of the invention are set forth in the description below. Other features or advantages of the present invention will be apparent from the drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure. In the drawings:

FIGS. 1A-1E include diagrams showing targeting of gene amplification in cancer via triplex formation. FIG. 1A: a schematic illustration showing a drug design scheme. Targeting the HER2 gene on a genomic level using DNA-binding molecules provides a novel therapeutic option to directly manipulate the DNA damage response pathways to specifically attack the HER2-amplified tumor. Triplex-induced DNA damage will only provoke apoptosis when multiple triplex structures are formed, while nucleotide excision repair (NER)-dependent repair prevails in the presence of one or two structures. FIG. 1B: a table showing the gene copy number characteristics of breast cancer cells lines[18]. FIG. 1C: a photo showing the western blot analysis of HER2 protein levels in breast cancer cell lines with varying gene copy number. FIG. 1D: a schematic illustration showing that TFOs bind as third strands in a sequence-specific manner within the major groove of duplex DNA at polypurine sites. The specificity of these molecules arises from the formation of base triplets via reverse Hoogsteen hydrogen bonds between the third strand and the polypurine strand of the duplex DNA. Results shown are from the use of TFOs HER2-1 and HER2-205, designed to bind to a polypurine sequence located either in the promoter or the coding region of the HER2 gene. FIG. 1E: photos of non-denatured metaphase chromosome spreads of MCF7 and BT474 breast cancer cells demonstrate chromosomal binding of TAMRA-HER2-205 (red) to its target site located on chromosome (chr.) 17 (green).

FIG. 2A: Representative images of neutral comet assays performed 24 h after HER2-205 treatment in MCF7 and BT474 cells. FIG. 2B: a chart showing the quantification of triplex-induced DNA double strand breaks using the neutral comet assay as measured by tail moment in multiple breast cancer cell lines. FIG. 2C: a chart showing that triplex-induced DNA damage increases in cell lines containing multiple copies of the HER2 gene. FIG. 2D: a chart showing the frequency of cells with more than 5 γH2AX foci per nuclei following 24 h HER2-205 treatment. FIG. 2E: Representative images of HER2-205 induced 53BP1 (green) and γH2AX (red) foci in nuclei (blue) compared to MIX24 24 h post-treatment in BT474 cells. FIG. 2F: a chart showing the analysis of triplex-induced apoptosis as measured by Annexin-V staining in breast cancer cell lines 24 h post TFO-treatment. FIG. 2G: a chart showing that the level of triplex-induced apoptosis increases with gene copy number. FIG. 2H: a chart showing the analysis of triplex-induced apoptosis in HER2-positive ovarian cancer cells as measured by Annexin V staining 48 h post-treatment. ** denotes $p<0.0001$, * denotes $p<0.001$, ** denotes $p<0.01$, and * denotes $p<0.05$ FIGS. 3A-3I include diagrams showing triplex-induced DNA damage and activation of apoptosis in several HER2-positive breast and ovarian cancer cell lines. "UT"=untreated cells. "Mock"=cells with transfection reagent only. "MIX24"=cells treated with control mixed sequence oligonucleotide, MIX24. "HER2-1"=HER2-1-treated cells. "HER2-205"=HER2-205-treated cells.

FIG. 4D: a Kaplan-Meier plot of the percentage of tumors smaller than three times baseline size. Baseline size was defined as tumor size on the first day of treatment [Day 28 in (FIG. 4A) and Day 21 in (FIG. 4B) and (FIG. 4C)]. FIG. 4E: images showing a histopathologic analysis of BT474 tumor sections from mice 24 h after treatment with a single dose of HER-2-205 (20 mg/kg body weight) or vehicle. Haematoxylin and eosin (H&E), caspase 3, HER2, Ki67 stain at 4× magnification. Scale bar=10 μm. FIG. 4F: an image showing a higher magnification of FLU tumor section from HER2-205 treatment specimen. FIG. 4G: a Kaplan-Meier plot of the percentage of SKOV3 ovarian cancer tumors smaller than three times baseline size. Mice were treated with 3 doses of HER2-205 at a concentration of 20 mg/kg or cisplatin at a concentration of 10 mg/kg.

FIG. 5A: images showing a western blot analysis of the phosphorylation status of the DNA damage response proteins Chk1 and Chk2 following TFO treatment. FIG. 5B: images showing that the knockdown of the NER factor, XPD, in BT474 cells results in a decrease in the induction of apoptosis as measured by cleaved PARP and pH2AX Y142. pH2AX Y142 is an essential post-translational modification for the recruitment of pro-apoptotic factors to the tail of γH2AX. FIG. 5C: images showing that HER2-205 activates p53-independent apoptosis in HER2-positive BT474 cells. FIG. 5D: a chart showing the analysis of HER2 gene expression by RT-PCR and FIG. 5E: images showing that determination of HER2 protein levels and phosphorylation status using Western blot analysis provide evidence that HER2-205 achieves therapeutic activity using a mechanism that is independent of HER2 cellular function. FIG. 5F: a schematic illustration of molecular mechanism of gene-targeted apoptosis. TFO binding in the major groove of duplex DNA causes a distortion of the double helix, which can induce DNA replication fork collapse and induction of DNA double strand breaks (DSBs). DNA damage response activates an XPD-dependent but p53-independent apoptotic pathway.

FIG. 6A: a chart showing the quantification of phosphorylated ATM by flow cytometry following treatment with HER2-205. Western blot analysis of the phosphorylation status of HER family receptors (FIG. 6B) HER3, (FIG. 6C) HER4, and (FIG. 6D) EGFR (HER1) multiple breast cancer cell lines following HER2-205 treatment.

FIG. 8A includes a chart showing TFOs targeting non-coding regions of the HER2 gene can induce DNA DSBs. The chart shows quantification of triplex-induced DSBs using the neutral comet assay as measured by tail moment. Triplex-induced DNA damage was assessed 24 hours post treatment. FIG. 8B includes a chart showing that TFOs targeting non-coding regions of the HER2 gene can induce apoptosis. The chart shows analysis of triplex-induced apoptosis as measured by Annexin-V staining 24 hours post-treatment in BT474 cells. ** denotes $p<0.0001$, * denotes $p<0.001$, ** denotes $p<0.01$, and * denotes $p<0.05$.

DETAILED DESCRIPTION

Figure 1D:
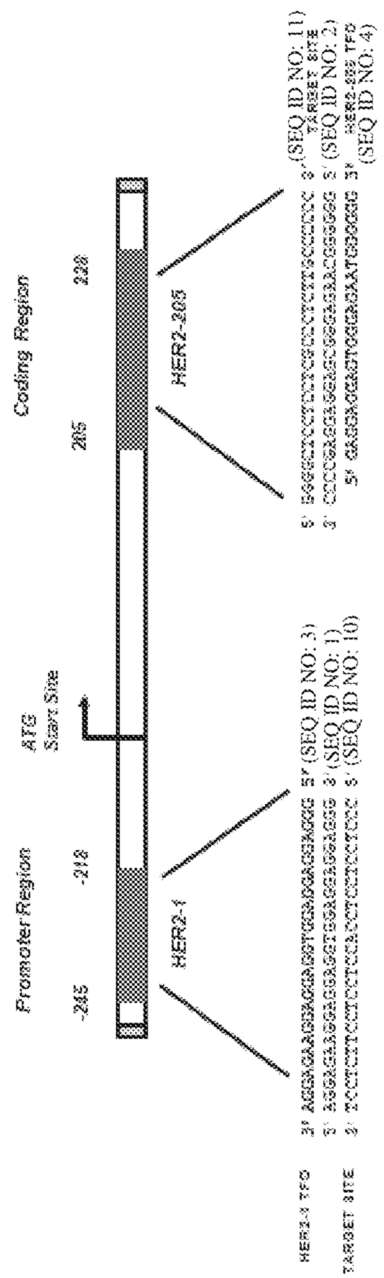

Described herein is a method of reducing, in a population of cells, the number of p53-depleted cancer cells in which a HER2 gene is amplified and agents useful to reduce the number of p53-depleted cancer cells comprising an amplified HER2 gene. In specific embodiments, the agents are triplex-forming oligonucleotides (TFOs) that are targeted to a polypurine site in an amplified HER2 gene in p53-depleted cancer cells.

In one embodiment, the method comprises contacting a population of cells, such as tissue, comprising p53-depleted cancer cells in which a HER2 gene is amplified with triplex forming oligonucleotides (TFOs) targeted to a polypurine target site in the HER2 gene(s), under conditions under which the TFOs enter the p53-depleted cancer cells in sufficient quantity to induce apoptosis.

Advancements in DNA sequencing technology have not only revealed commonly mutated and deleted genes across cancer types, but also enabled identification of amplified cancer-promoting genes[8]. These amplified genes include epigenetic regulators, cell cycle-associated genes, and genes linked to signaling pathways, such as the EGFR and HER2 genes[9]. Described herein is an approach for targeted therapeutics that can be used in the treatment of p53-depleted cancers characterized by gene amplification and that has limited toxicity to normal tissue. The limited toxicity is at least due to the localized effect and targeting of the TFOs to cells that have HER2-amplified genes and thus are likely to be the cancerous cells in the tissue. Described herein are agents and methods demonstrating that manipulation of DNA damage response is as effective in its anticancer activity as targeting the individual overexpressed protein product.

Provided herein are triplex-forming oligonucleotides (TFOs, also referred to as triplex-inducing oligonucleotides) for the induction of p53-independent apoptosis. TFOs are molecules that function as sequence-specific gene targeting/modification tools. Without wishing to be bound by theory, it has been shown that the TFOs bind to the major groove of duplex DNA and are restricted to sites with purines (also referred to as polypurine sites) on one strand and pyrimidines on the other.

HER2 Gene Amplification and NER-Dependent Repair

Gene amplification is observed in a broad spectrum of cancers, contributing not only to incipient cancer development, but also to the development of drug resistance. HER2 gene amplification (amplification of human epidermal growth factor receptor 2-encoding gene) is observed in a vast majority of cancers. Cancers with HER2 gene amplification or overexpression of the HER2 protein are sometimes referred to as HER2-positive cancers. Non-limiting examples of such cancers include breast cancer, ovarian cancer, colorectal cancer, gastric cancer, lung cancer, and endometrial cancer. HER2 gene amplification has been identified in about 25% of breast cancers.

Disclosed herein are TFOs targeted to specific regions of the HER2 gene. These TFOs can be utilized for a p53-independent cancer therapy. There are several polypurine sites in the HER2 gene that are susceptible to triplex formation. Binding of TFOs to the HER2 gene major groove regions on the HER2 gene) causes DNA perturbation that can impede replication fork progression, resulting in fork collapse and helix distorting structures (e.g., lesions or, more specifically, DNA double strand breaks (DSBs))[14]. Under normal circumstances (e.g., low HER2 gene copy levels), these helix distorting structures trigger the nucleotide excision repair (NER) pathway, which repairs the helix distorting structures. This ability of the NER pathway to resolve low levels of triplex-induced DNA damage allows normal cells to tolerate the formation of a few triplexes[16,17]. In contrast, if there is HER2 gene amplification and consequently high levels of triplex formation, NER-dependent DNA repair is ineffective and instead apoptosis triggered[15]. HER2 gene amplification in cancers, such as breast cancers, provides an opportunity to test the efficacy of TFOs as an apoptosis-inducing agent in cancer cells, but not in healthy cells, which lack HER2 amplification (FIGS. 1A-1C).

XPD, a transcription factor II H (TFIIH) subunit, plays a key role in this NER pathway by operating as a 5'-3' helicase to unzip the DNA. In instances of high DNA damage (or high triplex formation), XPD is required for p53-mediated apoptosis (see U.S. Pat. No. 9,587,238, the relevant disclosures of which are herein incorporated as reference). Previous studies established that m cases of excess DNA damage, an apoptotic pathway is initiated that is dependent on the presence of both XPD and p53. This, in part, explains the chemotherapeutic drug resistance and the difficulty in treating p53-defective conditions.

P53 Tumor Suppressor

Disclosed herein are methods and compositions for inducing apoptosis in p53-depleted cells comprising an amplified HER2 gene. P53 (also referred to as TP53 or p53 tumor suppressor) is a gene on the $17^{th}$ b chromosome (17p13.1) that encodes p53 protein (also referred to as TP53 or tumor protein). The protein is a regulator in the cell cycle and plays the role of a tumor suppressor. The p53 tumor suppressor regulates pro-apoptotic pathways in response to severe DNA damage. Under normal, non-pathological conditions, p53 expression is low. DNA damage and related signals upregulate its expression to initiate growth arrest, DNA repair, and, in extreme cases, apoptosis. Typically, growth arrest inhibits replication of damaged DNA; however, in cancerous cells this is bypassed. As explained herein, gene amplification manifests in cancerous cells and can result in ineffective DNA repair (for example, ineffective NER-mediated DNA repair). In such cases, p53 is relied on for apoptosis of the damaged cells.

Mutations in p53 are correlated with a broad spectrum of aggressive cancers and have been implicated in as many as 50% of all human tumors, highlighting the importance of this gene and the impact of a p53-independent chemotherapeutic approach. Over 50% of human cancers exhibit chemotherapeutic resistant phenotypes due to loss of function p53 mutations, which lead to an inability to trigger apoptosis. Previous studies attempted to address cancer treatment in p53-defective conditions by upregulating wild-type p53 or augmenting the activity of wild-type p53 (Smith and Seo, *Mutagenesis* 17(2), 149-156, 2002). Additional strategies to overcome this challenge include attempts to modify the p53 gene through gene editing, reactivate p53 genes with chemotherapeutic drugs, or suppress p53 mutant aggregation. These strategies have had limited success.

The term "p53-depleted" refers to cells, such as cancer cells, in which p53 is reduced, lacking or mutated. In some embodiments, a p53-depleted cancer cell is a cell that does not express p53. It can also refer to significantly decreased p53 expression under conditions under which p53 is typically upregulated (e.g., in response to a DNA lesion). Mutations in p53 have been shown to give rise to different isoforms, some of which give rise to tissue-specific cancers. The term "p53-depleted" also includes cells, such as cancer cells, in which the p53 gene has a mutation (e.g., loss of function mutation, gain of function mutation, etc.) and produces a protein that is dysfunctional (e.g., displays no or reduced function). This may also occur through the production of a truncated p53 protein that is dysfunctional. Most p53 mutations are missense mutations. In some embodiments, the p53-mutated cell is a homozygote mutant. In some embodiments, the p53-mutant cell is a heterozygote, carrying a wild-type p53 allele and a mutant p53 allele. Previous studies have shown that in some heterozygote cases, the mutant allele functions in a dominant negative manner, suppressing the expression of the wild-type allele. Loss of wild-type p53 and p53 mutations have been shown to occur in both early and late tumorigenesis. Some p53 mutations, referred to as gain-of-function p53 mutations, result in p53 mutant proteins that have additional oncogenic properties and promote cancer progression (Rivlin et al *Genes & Cancer* 2(4):466-474, 2011).

Triplex Forming Oligonucleotides (TFOs)

Triplex-forming oligonucleotides (TFOs) form triplexes, which are DNA structures comprised of an additional RNA or DNA binding sequence. Without wishing to be bound by theory, they are believed to bind in the major groove of duplex DNA. Purine motif TFOs (comprised of G and A) form G*G:C and A*A:T triplets and bind in antiparallel orientation, via reverse Hoogsteen base pairing, with regard to the purine strand of the duplex. In contrast, pyrimidine motif TFOs (C/T) form triplexes in parallel orientation, via forward Hoogsteen alignment, and form $C^{+}$*G:C and T*A:T triplets. Mixed purine and pyrimidine TFOs bind in either parallel or antiparallel orientation and form G*G:C and T*A:T triplets. (Maldonado, R., et al. *RNA* 24(3): 371-380, 2018 and Basye, J., et al. *Nucleic acids research* 29(23): 4873-4880, 2001).

Applications of HER2 Targeted TFOs

As described, HER2-targeted TFOs trigger an alternative pathway, a p53-independent apoptotic pathway. HER2-targeted TFOs induce copy number dependent DNA double strand breaks (DSBs) and activate apoptosis in HER2 gene amplified cancer cells and human tumor xenografts via a mechanism that is independent of HER2 cellular function as well as independent of p53. In specific embodiments, HER2-targeted TFOs, HER2-1 (SEQ ID NO:3), HER2-205 (SEQ ID NO:4), HER2-5922-2 (SEQ ID NO:7), and HER2-40118 (SEQ ID NO: 8), trigger p53-independent apoptosis in cancer cells comprising amplified HER2 gene.

In some embodiments, the HER2-targeted TFOs target polypurine target sites in the promoter region of the HER2 gene (e.g., the HER2-1 TFO (SEQ ID NO: 3)). In some embodiments, the HER2-targeted TFOs target polypurine target sites in the coding region of the HER2 gene (e.g., the HER2-205 TFO (SEQ ID NO: 4)). In some embodiments, the HER2-targeted TFOs target introns or non-coding regions of the HER2 gene. For example, the HER2-5922-2 TFO (SEQ ID NO: 7) targets a site within intron 2 of the HER 2 gene, and the HER2-40118 (SEQ ID NO: 8) TFO targets intron 19 of the HER2 gene.

Disclosed herein is a method of reducing, in a population of cells, the number of p53-depleted cancer cells comprising an amplified HER2 gene. As described, this method can be carried out in a population of cells, such as in a tissue or organ. As used herein, the term “reducing” refers to decreasing the number of living cells by inducing apoptosis in the cells. The reduction could decelerate rapid cell growth or decelerate hyperplasia, which are two common characteristics of cancerous cells.

The methods disclosed herein includes contacting p53-depleted cancer cells comprising amplified HER2 gene with triplex-forming oligonucleotides (TFOs) targeted to a polypurine target site in the amplified-HER2 gene.

In some embodiments, the TFOs are polypurine TFOs. Polypurine TFOs are rich in adenine and/or guanine bases, and, without wishing to be bound by theory, are believed to bind to the major groove of their polypurine target sites in an antiparallel fashion. As used, the term “polypurine TFO” refers to purine motif TFOs or TFOs rich in purines (adenine and/or guanine bases). As used, the term “polypurine target site” refers to a DNA duplex having a strand rich in purines (adenine and/or guanine bases). The terms “polypurine target strand” and “polypurine strand” refer to the strand in the polypurine target site that is rich in purines (adenine guanine or both adenine and guanine bases). In some embodiments, a sequence is referred to as “rich in purines” when 50%, 55%, 60%, 65%, 70%, 75%, 80%, 85%, 90%, 95%, 98%, 99% or more of its nucleotides have adenine and/or guanine bases.

An example, of a polypurine target site identified in the promoter region of the HER2 gene is a DNA duplex having the sequence 5'-AGGAGAAGGAGGAGGTGGAGGAGGAGGG-3'(SEQ ID NO:1) bound to 5'-CCCTCCTCCTCCACCTCCTCCTTCTCCT-3'(SEQ ID NO:10). Another example of a polypurine target site identified in the coding region of the HER2 gene is a DNA duplex having the sequence 3'-CCCCGAGGAGGAGCGGGAGAACGGGGGG-5'(SEQ ID NO:2) bound to 5'-GGGGCTCCTCCTCGCCCTCTGCCCCCC-3'(SEQ ID NO:11). (FIG. 1B).

Figure 7:
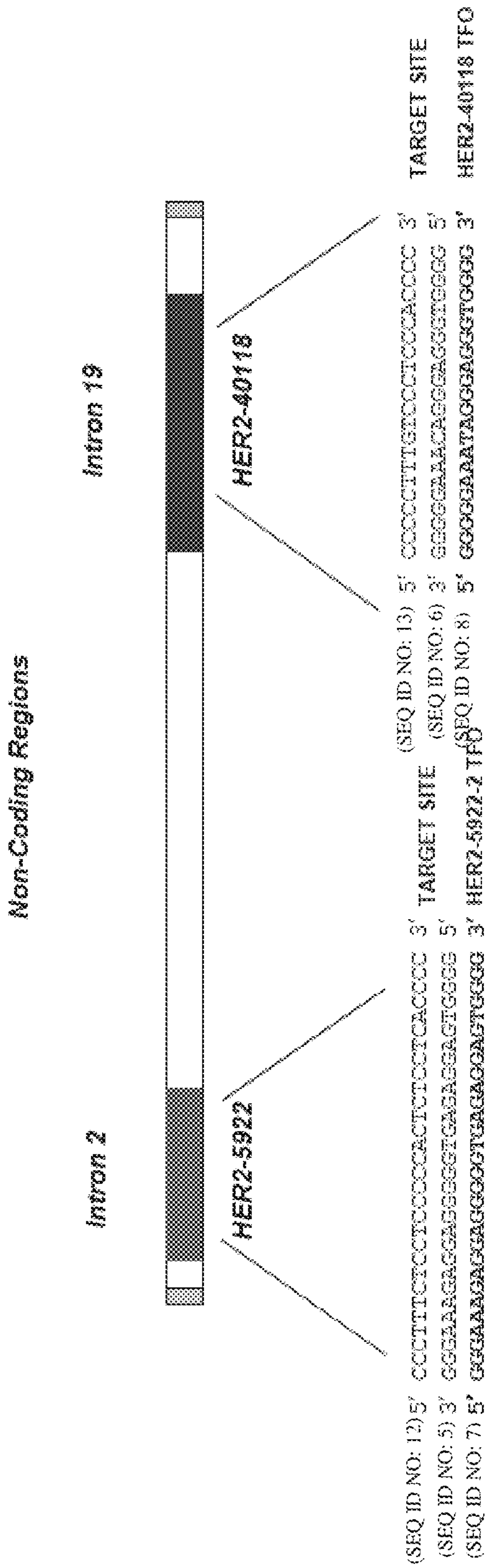
FIG. 7 includes a schematic illustration showing TFOs that are designed to bind to polypurine sites in non-coding regions of the HER2 gene, which is located on chromosome 17. Two TFOs, HER2-5922-2 and HER2-40118, were designed to target the introns of the HER2 gene.

Another example of a polypurine target site identified in the non-coding region of the HER2 gene is a DNA duplex having the sequence 3'-GGGAAAGAGGAGGGGGTGAGAGGAGTGGGG-5'(SEQ ID NO: 5) bound to 5'-CCCTTTCTCCTCCCCCACTCTCCTACCCC-3'(SEQ ID NO: 12). Another example of a polypurine target site identified in the non-coding region of the HER2 gene is a DNA duplex having the sequence 3'-GG-5'(SEQ ID NO: 6) bound to 5'-CCCCCTTTGTCCCTCCCACCCC-3'(SEQ ID NO: 13). (FIG. 7).

Formation of the triplex after introduction of a TFO occurs via reverse Hoogsteen hydrogen bonds between the third strand (TFO) and the polypurine strand of the duplex.

In some embodiments, a TFO has a nucleotide sequence that is complementary to SEQ ID NOs: 10, 11, 12 and 13 and/or binds to at least 13 nucleotides in a polypurine target strand, such as at least 13 nucleotides in SEQ ID NO:1, SEQ ID NO:2, SEQ ID NO: 5 or SEQ ID NO: 6. In some embodiments, a TFO binds to 13, 14, 15, 16, 17, 18, 19, 20, 21, 22, 23, 24, 25, 26, 27, 28, 29 or 30 nucleotides in a polypurine, target strand. TFOs can bind to contiguous or non-contiguous nucleotides in a polypurine target site. The TFOs described herein can be any TFO sequence that is targeted to a polypurine target site in a HER2 gene, for example, polypurine target sites SEQ ID NO:1, SEQ ID NO:2, SEQ ID NO: 5 or SEQ ID NO: 6. In some embodiments, the TFOs are at least 13 nucleotides in length. In some embodiments, the TFOs range from 13 to 30 nucleotides in length. For example, the TFOs can be 13, 14, 15, 16, 17, 18, 19, 20, 21, 22, 23, 24, 25, 26, 27, 28, 29, or 30 nucleotides in length. In further embodiments, the TFOs are shorter (e.g., 8, 9, 10, 11, or 12 nucleotides).

Examples of HER2-targeted TFOs are HER2-1 (5'-GGGAGGAGGAGGTGGAGGAGGAAGAGGA-3'; SEQ ID NO:3), HER2-205 (5'-GAGGAGGAGTGGGAGAATGGGGGG-3'; SEQ ID NO:4), HER2-5922-2 (5'-GGGAAAGAGGAGGGGGTGAGAGTGGGG-3'; SEQ ID NO: 7), and HER2-40118 (5'-GGGGGAAATAGGGAGGGTGGGG-3'; SEQ ID NO: 8). HER2-1 hybridizes to SEQ ID NO:1, under physiological conditions. HER2-205 hybridizes to SEQ ID NO:2, under physiological conditions. HER2-5922-2 hybridizes to SEQ ID NO: 5, under physiological conditions. HER2-40118 hybridizes to SEQ ID NO: 6, under physiological conditions (FIGS. 1D and 7).

As used, the term “complementary” refers to the capacity for precise pairing (also referred to as hybridization) between two nucleotides. For example, if a nucleotide at a certain position of an oligonucleotide is capable of hydrogen bonding with a nucleotide at a corresponding position of a target RNA, then the nucleotide of the oligonucleotide and the nucleotide of the target RNA are complementary to each other at that position. As understood by one of ordinary skill in the art, for complementary base pairings, adenosine-type bases (A) are complementary to thymidine-type bases (T) or uracil-type bases (U), cytosine-type bases (C) are complementary to guanosine-type bases (G), and universal bases such as 3-nitropyrrole or 5-nitroindole can hybridize to and are considered complementary to any A, C, U, or T. In some embodiments, the methods and agents of the present disclosure can include Inosine (I). Inosine has also been considered in the art to be a universal base and is considered complementary to A, C, U or T.

In some embodiments, the TFO is a nucleotide sequence that is at least 90% identical to SEQ ID NO:3, SEQ ID NO:4, SEQ ID NO: 7 or SEQ ID NO: 8. As used herein, the term "identity" or "identical" refers to sequence identity, which refers to two nucleotides being identical. In some embodiments, the TFO is a nucleotide at least 90%, 91%, 92%, 93%, 94%, 95%, 96%, 97%, 98%, 99% or 100% identical to SEQ ID NO:3, SEQ ID NO:4, SEQ ID NO: 7 or SEQ ID NO: 8.

The sequence on a HER2 gene to which a TFO is targeted is referred to as a "target sequence." For example, a TFO that is targeted to a polypurine site is one that hybridizes to that polypurine site under physiological conditions, such as in the case of in vivo administration or treatment. "Targeted" can also refer to a TFO that specifically hybridizes to a polypurine site (partially or completely). For example, the TFO hybridizes to a sequence in the target sequence or target sequence, but does not hybridize to any other (off-target) nucleotide sequence within the cell and would not hybridize to a sequence within a cell that lacks the polypurine site, under physiological conditions.

In the methods of the present disclosure, TFOs are contacted with p53-depleted cells that comprise amplified HER2 gene by a variety of approaches, such as by administering TFOs to an individual in need of a reduction in a population of p53-deficient cells that comprise amplified HER2 gene. For example, TFOs in an appropriate delivery vehicle can be administered to an individual with cancer in which cancer cells are p53 depleted and comprise amplified HER2 gene. The TFOs are contacted with such cells by any manner and under conditions that result in entry into cells in the individual. For example, TFOs can be introduced into an individual by injection, infusion, or any delivery method, such as those described further below.

In some embodiments of the present disclosure, the TFOs are administered to an individual who has been screened for a p53 mutation, has HER2-positive cancer cells, and thus has been identified as a candidate for this p53-independent TM-treatment. Non-limiting examples of methods for identifying an individual with p53 mutations include genetic testing of the DNA found in sera or other body fluids (see Rivlin et al., *Genes & Cancer* 2(4):466-474, 2011, the relevant disclosures of which are herein incorporated as reference).

In some embodiments, the methods of the present disclosure are for the treatment of p53-mutated cancers. Non-limiting examples of such p53-mutated cancers include breast cancer, ovarian cancer, renal carcinoma, lung cancer, colon carcinoma, hepatocellular carcinoma, prostate cancer, bladder cancer, and pancreatic neoplasia. The methods of the present disclosure can include administering the TFOs herein to the cells of the aforementioned cancers (e.g., breast cancer cells, ovarian cancer cells, renal cell carcinoma cells, lung cancer cells, colon cancer cells, colorectal cancer cells, gastric cancer cells, and endometrial cancer cells).

Li-Fraumeni Syndrome Application

In some embodiments, the present disclosure includes methods and compositions for the treatment of an individual with Li-Fraumeni Syndrome (LFS) or treatment of a cancer in an individual with LFS. LFS is a cancer predisposition syndrome characterized by germline, mutations of p53 (Smith and Seo, *Mutagenesis* 17(2), 149-156, 2002). Individuals with LFS are susceptible to a broad spectrum of cancers and are susceptible to early onset of these cancers. Of the spectrum of Li-Fraumeni-associated tumors, breast cancer, sarcomas of the soft tissues and bone, acute leukemias, and brain tumors are among the most common (Nichols et al., *Cancer Epidemiology and Prevention Biomarkers* 10(2): 83-87, 2001, the relevant disclosures of which are herein incorporated by reference). The lifetime risk of an LFS patient to develop cancer has been estimated to be as high as 90%. Non-limiting examples of types of cancer commonly found in families with ITS include osteosarcoma (bone cancer), soft-tissue sarcoma, acute leukemia, breast cancer, brain cancer, adrenal cortical tumors, and acute leukemia.

In some embodiments, an individual is screened for HER2 gene amplification before administration of the TFO. Methods for detection of gene amplification are known in the art. Non limiting examples of these methods include conventional cytogenetics, Southern blotting, quantitative PCR, fluorescence in situ hybridization (FISH), comparative genomic hybridization (CGH), and microarray technology.

Due to the limited toxicity associated with the described TFOs, in alternative embodiments, a TFO targeted to at least one sequence in HER2 gene can be administered to an individual diagnosed with cancer to induce p53 independent apoptosis in p53-depleted cells comprising an amplified HER2 gene prior to or without screening for HER2 gene amplification.

Chemical Modifications to TFOs

In some embodiments, the TFOs have backbone modifications. Unmodified purine TFOs bind well under physiologic conditions, but binding efficiency can sometimes be inhibited at physiologic $K^+$ conditions. Backbone modifications can augment the binding efficiency of such TFOs. Various modifications for purine TFOs are disclosed in Knauert and Glazer, Human Molecular Genetics 10(20): 2243-2251, 2001, the relevant disclosures of which are herein incorporated by reference. Non-limiting examples of backbone modifications to the TFOs include phosphorothioates, phosphorodithioates, methylphosphonates, phosphoramidates, boranophosphate oligos, polyamides, methylene (methylimino) linkages, morpholine oligos, and combinations thereof. TFOs with polyamide backbone modifications bind to the minor groove of the DNA duplex, rather than the major groove.

Combination Therapies

Disclosed herein are methods of administering TFOs in sufficient quantity to induce p53-independent apoptosis in p53-depleted cells comprising an amplified HER2 gene. In some embodiments, one type of TFO (e.g., either HER2-1 or HER2-205) is administered. In some embodiments, TFOs of more than one type are administered (e.g., a mixture of TROs, mixture of HER2-1 and HER2-205, etc.). Herein, reference to "administering TFOs" can also refer to the administration of TFOs of more than one type.

In some embodiments, the one type of TFO is administered in combination with at least one non-TFO (e.g., a non-TFO anticancer agent). In some embodiments, more than one type of TFO is administered with at least one non-TFO (e.g., a non-TFO anticancer agent). An anticancer agent that is not a TFO can be, for example, a protein, a nucleic acid, a small molecule, or a drug for the treatment of cancer. This anticancer agent can have any anticancer effect on the population of cells that it is administered to including, but not limited to, is cytotoxic, apoptotic, anti-mitotic anti-angiogenesis or inhibition of metastasis effect. This anticancer agent can also affect DNA damage response (e.g., a DNA repair inhibitor). In some embodiments, the second anticancer agent is a drug directed against overexpressed protein products.

Anticancer agents include, for example, antimetabolites, inhibitors of topoisomerase I and II, alkylating agents and microtubule inhibitors (e.g., taxol). Non-limiting examples of anticancer agents include adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliotts B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; valtorcitabine, (monoval LDC); vinblastine; vinorelbine; zoledronate; and mixtures thereof, among others (see U.S. Pat. No. 9,643,922, the relevant disclosures of which are herein incorporated by reference).

Non-limiting examples of anticancer agents include oestrogen receptor modulators, androgen receptor modulators, retinoid receptor modulators, cytotoxic agents, antiproliferative agents, prenyl-protein transferase inhibitors, HMG-CoA reductase inhibitors, reverse transcriptase inhibitors and further angiogenesis inhibitors.

Non-limiting examples of retinoid receptor modulators include bexarotene, tretinoin, 13-cis-retinoic acid, 9-cis-retinoic acid, .alpha.-difluoromethylornithine, ILX23-7553, trans-N-(4'-hydroxyphenyl)retinamide and N-4-carboxyphenylretinamide (see U.S. Pat. No. 10,093,623, the relevant disclosures of which are herein incorporated by reference).

Non-limiting examples of cytotoxic agents include tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032, the relevant disclosures of which are herein incorporated by reference).

Non-limiting examples of antiproliferative agents include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-[N2-[2(E), 4(E)-tetradecadienoyl]-glycylamino]-L-glycero-B-L--mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab (for examples, see U.S. Pat. No. 6,069,134, the relevant disclosures of which are herein incorporated by reference).

The first drugs directed against overexpressed protein products were major breakthroughs in cancer therapeutics. For example, trastuzumab (HERCEPTIN®) targets the HER2 receptor tyrosine kinase, which is overexpressed in about 25% of breast tumors due to gene amplification[10]. Trastuzumab works, at least in part, by disrupting HER2 signaling, which results in cell cycle arrest and suppression of cell growth and proliferation[11]. While trastuzumab has proven to be effective in prolonging the survival of HER2-positive breast cancer patients, primary and acquired drug resistance limits overall success rates. Similar problems hamper the long-term efficacy of other cancer drugs, including the tyrosine kinase inhibitors gefitinib (IRESSA®) and erlotinib (TARCEVA®), which target EGFR gene amplification in breast, colorectal, and lung cancer[12,13].

Methods of Administering TFOs

The TFOs of the present disclosure may be administered to an individual by any route or in any delivery vehicle.

In some embodiments, the TFOs are administered in a delivery vehicle (e.g., lipid-based nanoparticles). The TFOs can be conjugated to the lipid-based nanoparticles. Alternatively, the TFOs can be encapsulated in the lipid-based nanoparticles. One example of lipid-based nanoparticles is lipid nanoparticles that contain a solid lipid core matrix with the ability to solubilize lipophilic molecules. The term "solid" refers to a nanoparticle that is solid at room temperature and atmospheric pressure. The lipid nanoparticles can have a nanostructure core (solid or hollow) and a lipid layer. The diameter of the core can be less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some embodiments, the core is less than 1000 nm. In some embodiments, the core is 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 120 nm, 140 nm, 160 nm, 180 nm, 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, or 500 nm in diameter.

The lipid nanoparticle can be a solid lipid nanoparticle or a polymeric nanoparticle. Methods for making solid liquid nanoparticles are well-established in the art (see, for example, Casco, M. R., Nanoparticelle Lipidiche Solide Quali Sisterni Terapeutici Colloidali, *NCF* nr. 7: 71-73, 1996; Kozariara et al., *Pharmaceutical Research,* 20(11); 1772, 2003; and Lockman et al., *Journal of Controlled Release,* 93:271-282, 2003, the relevant disclosures of which are herein incorporated by reference).

In a polymeric lipid nanoparticle, the polymer can be any ionic or ionizable polymer or copolymer known to those of skill in the art including polymers and copolymers of, for example, polyglycine, polyethylene glycol, heparin, hydroxypropylmethylcellulose, hydroxyethylcellulose, hydroxypropylcellulose, polyvinylpyrrolidone, polyvinyl alcohol, poly-beta amino esters (PBAEs), methacrylic acid copolymers, ethyl acrylate-methyl methacrylate copolymers, and mixtures thereof. In some embodiments, the first functionalized polymer can be poly(glycolic acid), poly (lactic acid) (PLA), or copolymers thereof, such as poly(D, L-lactide-co-glycolide), or mixtures thereof.

In some embodiments, the TFOs are delivered using poly(lactic-co-glycolic acid) (PLGA) nanoparticles or PLA nanoparticles. In some embodiments, the PLGA nanoparticles or PLA nanoparticles are loaded with the TFOs of the present, disclosure. In some embodiments the nanoparticles include an agent conjugated to their surface, such as polyethylene glycol (PEG) and hyperbranched polyglycerols (HPG).

In some embodiments, the lipid nanoparticles include cationic lipids or anionic lipids. Alternatively, the lipid nanoparticles can include neutral lipids. Non-limiting examples of cationic lipids include 3β-(N—(N',N'-dimethylaminoethane)-carbamoyl)cholesterol hydrochloride (DC-Chol); 1,2-dioleoyl-3-trimethylammonium-propane (DOTAP); 1,2-dioleoyl-3-dimethylammonium-propane (DODAP); dimethyldioctadecylammonium bromide salt (DDAB); 1,2-dilauroyl-sn-glycero-3-ethylphosphocholine chloride (DL-EPC); N-(1-(2, 3-dioleyloyx) propyl)-N—N—N-trimethyl ammonium chloride (DOTMA); N-(1-(2, 3-dioleyloyx) propyl)-N—N—N-dimethyl ammonium chloride (DODMA); N,N-dioctadecyl-N,N-dimethylammonium chloride (DODAC); N-(1-(2,3-dioleyloxy)propyl)-N-2-(sperminecarboxamido)ethyl)-N,N-dimethylammonium trifluoracetate (DOSPA); 1,2-dimyristyloxypropyl-3-dimethylhydroxyethyl ammonium bromide (DMRIE); dioctadecylamidoglycylspermine (DOGS); neutral lipids conjugated to cationic modifying groups; and combinations thereof. Non-limiting examples of anionic lipids include fatty acids such as oleic, linoleic, and linolenic acids; cholesteryl hemisuccinate; 1,2-di-O-tetradecyl-sn-glycero-3-phospho-(1'-rac-glycerol) (Diether PG); 1,2-dimyristoyl-sn-glycero-3-phospho-(1'-rac-glycerol) (sodium salt); 1,2-dimyristoyl-sn-glycero-3-phospho-L-serine (sodium salt); 1-hexadecanoyl,2-(9Z,12Z)-octadecadienol-sn-glycero-3-phosphate; 1,2-dioleoyl-sn-glycero-3-(phospho-rac-(1-glycerol)) (DOPG); dioleoylphosphatidic acid (DOPA); and 1,2-dioleoyl-sn-glycero-3-phospho-L-serine (DOPS); anionic modifying groups conjugated to neutral lipids; and combinations thereof. Non-limiting examples of neutral lipids include phosphatidylcholine (PC), phosphatidylethanolamine, ceramide, cerebrosides, sphingomyelin, cephalin, cholesterol, diacylglycerols, glycosylated diacylglycerols, prenols, lysosomal PLA2 substrates, and N-acylglycines. Additional examples of lipids and lipid components can be found in U.S. Pat. No. 9,833,416.

The lipid nanoparticles can comprise surfactants anchor emulsifiers. Non-limiting examples of surfactants include phospholipids, phosphatidylcholines, TWEENs, Soy lecithin, egg lecithin (Lipoid E 80), phosphatidylcholine, poloxamer 188, 182, and 407, poloxamine 908, Tyloxapol, polysorbate 20, 60, and 80, sodium cholate, sodium glycocholate, taurocholic acid sodium salt, taurodeoxycholic acid sodium salt, butanol, butyric acid, dioctyl sodium sulfosuccinate, and monooctylphosphoric acid sodium. Non-limiting examples of emulsifiers include cationic phospholipid or non-ionic surfactant. Examples of cationic surfactant include, but are not limited to, 1,2-dimyristoyl-3-trimethylammonium-propane (DMTAP), 1,2-dipalmitoyl-3-trimethylammonium-propane (DPTAP), 1, 2-distearoyl-3-trimethylammonium-propane (DSTAP), 1,2-dioleoyl-3-trimethylammonium-propane (DOTAP), 1,2-dimyristoyl-3-dimethylammonium-propane (DMDAP), 1,2-dipalmitoyl-3-dimethylammonium-propane (DPDAP), 1,2-dilauroyl-3-dimethylammonium-propane (DLDAP), 1,2-distearoyl-3-dimethylammonium-propane (DSDAP), dimethyldioctadecylammonium chloride (DDAB), N-[1-(1, 2-dioleoyloxy)propyl]-N,N,N-trimethylammonium chloride (DOTMA) and 1,2-dioleoyl-3-ethylphosphocholine (DOEPC). Examples of non-ionic surfactants include, but are not limited to poloxamers, sorbitan esters (Span), polyoxyethylene-sorbitan fatty acid esters (Tween) and polyoxyethylene ethers (Brij).

In certain embodiments, the lipid comprises one or more of: a) cationic or anionic lipids or surfactants; b) neutral lipids or surfactants; c) cholesterol; and d) PEGylated lipids or surfactants.

Other non-limiting examples of lipid-based nanoparticles include liposomes, bolaamphiphiles, nanostructured lipid carriers (NLC), and monolayer membrane structures (e.g., archaeosomes and micelles). Methods of encapsulating agents in lipid nanoparticles are disclosed in Puri et al. *Critical Reviews in Therapeutic Drug Carrier Systems* 26(6):523-580, 2009, the relevant disclosures of which are herein incorporated by reference.

In some embodiments, the TFOs are conjugated to cholesterol to enhance delivery into cells. In some embodiments, the TFO are administered absent of a transport peptide or cell-penetrating peptide (CPP). In some embodiments, the TFOs are administered with a peptide, e.g., cell-penetrating peptides (CPPs), primary amphipathic peptides, such as MPG or Pep-1.

The administration of the TFOs can be directly to tissue in an individual. In some embodiments, the TFOs are delivered systemically. In some embodiments, the TFOs are delivered locally or intratumorally. In some embodiments, the TFOs are administered as an injection. As used, an injection can use different delivery routes. In some embodiments, the TFOs are administered intravenously or intraperitoneally. In some embodiments, the TFOs are administered intravenously, intradermally, intraarterially, intralesionally, intratumorally, intracranially, intraarticularly, intraprostatically, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, locally, inhalation (e.g., aerosol inhalation), injection, infusion, continuous infusion, localized perfusion bathing target cells directly, via a catheter, via a lavage, in creams, in lipid compositions (e.g., liposomes, lipid nanoparticles, etc.), or by other method or any combination of the forgoing as would be known to one of ordinary skill in the art (see, for example, Remingtons Pharmaceutical Sciences (1990), incorporated herein by reference).

In some embodiments, the TFOs are administered as a composition having a pharmaceutically acceptable carrier. In some embodiments, the pharmaceutically acceptable carrier comprises water or saline.

The term "pharmaceutically-acceptable carrier" refers to one or more compatible solid or liquid filler, diluents or encapsulating substances which are suitable for administration to a human or other subject contemplated by the disclosure. "Pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remingtons Pharmaceutical Sciences (1990), incorporated herein by reference). Except insofar as any conventional carrier is incompatible with the active ingredient, its use in the therapeutic or pharmaceutical compositions is contemplated.

The TFOs can be administered once, or alternatively they may be administered in a plurality of administrations. If administered multiple times, the compounds may be administered via different routes. For example, the first (or the first few) administrations may be made directly into the affected tissue while later administrations may be systemic.

In some aspects of the present disclosure, the term "individual" refers to a mammal. In some embodiments, individual refers to a human. Alternatively, individual can refer to a mammal, wherein the mammal is selected from a group including but not limited to non-human primates, cows, horses, pigs, sheep, goats, dogs, cats, rabbits, ferrets, and rodents. In some embodiments, the term "individual" is used to refer to a model of cancer. Non-limiting examples of models of cancer include p53-knockout mice, BALB/c mice injected with MDA-MB-453 cells, SKBR3 cells, BT474 cells, PEO1 cells, or SKOV3 cells, and LFS mouse models (engineered to express mutant p53).

As used herein, the term "sufficient quantity" refers to a "therapeutically effective amount" or "effective amount" that elicits a biological or medicinal response in a tissue, system, animal, individual or human that is being sought by a researcher, veterinarian, medical doctor or other clinician, in this case, the response would be a reduction (partial or total/complete) in the number of p53-depleted cancer cells comprising a HER2 gene by apoptosis. The appropriate response can be determined in vitro by trypsinization and cell counting (using methods established in the art). In vivo, the appropriate response from a therapeutically effective amount can be determined by measuring or visualizing (e.g., imaging) tumor size.

In some embodiments, the TFOs are administered to an individual in a dose of approximately 20 mg/kg. In some embodiments, the TFOs are administered to an individual in a dose of 5 mg/kg, 7 mg/kg, 9 mg/kg, 10 mg/kg, 12 mg/kg, 14 mg/kg, 16 mg/kg, 17 mg/kg, 18 mg/kg, 19 mg/kg, 20 mg/kg, 21 mg/kg, 22 mg/kg, 25 mg/kg, or 30 mg/kg. These disclosed amounts can be increased or decreased by one of ordinary skill in order to personalize a chemotherapeutic treatment plan based on an individuals stage of cancer, the size of tumor, the presence or absence of an adjuvant chemotherapeutic agent, etc.

TFO Use for Assays

In alternate embodiments, the method is an assay in which TFOs are contacted in vitro with p53-depleted cancer cells comprising a HER2 gene. As used, the term "contacting" refers to the use of TFOs in in vitro assays. The contacting can be through the transfection of cells with the TFOs in vitro. In some embodiments, the cells are cancer cells. In some embodiments, the cancer cells are contacted with TFOs under conditions under which the TFOs enter the p53-depleted cancer cells in sufficient quantity to induce apoptosis under the conditions of the in vitro assay.

Methods of transfection are well established in the arts and include chemical, biological, and physical methods. Chemical methods include, but are not limited to, calcium phosphate transfection, cationic polymer transfection polyethylenimine), lipofection, Oligofectamine™, DharmaFECT-1™, EUGENE®, and DEAE-Dextran-mediated transfection. Other methods of transfection include, but are not limited to, electroporation, microinjection, sonoporation, cell squeezing, impalefection, optical transfection, protoplast fusion, magnetofection™, and particle bombardment.

Non-limiting examples of cells that can be contacted by any of the TFOs described herein for in vitro assays, include carcinoma cells, lung cancer cells, colon cancer cells, human colon carcinoma cells, ovarian cancer cells, breast cancer cells, colorectal cancer, gastric cancer cells, and endometrial cancer cells. Additional non-limiting examples of cells that can be contacted by any of the TFOs described herein for in vitro assays, include MDA-MB-453 cells, SKBR3 cells, BT474 cells, PEO1 cells, or SKOV3 cells.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLES

Materials and Methods

Oligonucleotides. Oligonucleotides were synthesized by EDT with a 3'-amino modifier and purified by reverse-phase HPLC. The TFO, HER2-1 was designed to bind to the HER2 promoter and had the sequence 5'-GGGAGGAGGAGGTGGAGGAGGAAGAGGA-3'(SEQ ID NO: 3). HER2-205 was synthesized with the sequence 5'-GAG GAG GAG TGG GAG AAT GGG GGG-3'(SEQ ID NO: 4) and has been designed to bind to a polypurine sequence in the coding region of the HER2 gene. The control mixed-sequence oligonucleotide MIX24 has the following sequence: 5'-AGT CAG TCA GTC AGT CAG TCA GTC-3' (SEQ ID NO:9). Labeled oligonucleotide was synthesized with 5'-TAMRA modifications. HER2-5922-2 was synthesized with the sequence 5'-GGGAAAGAGGAGGGGGTGAGAGGAGTGGGG-3'(SEQ ID NO: 7). HER2-40118 was synthesized with the sequence 5'-GGGGGAAATAGGGAGGGTGGGG-3'(SEQ ID NO: 8).

Cell Lines and Transfections. Human breast cancer cell lines were obtained from ATCC and routinely tested for mycoplasma. The human cell lines, MDA-MB-453, SKBR3, and BT474 are HER2-amplified breast cancer cell lines. BT20 and MCF7 cells are non-amplified breast cancer cell lines. MCF-10A is a non-tumorigenic breast epithelial cell line. PEO1 and SKOV3 are human ovarian cancer cell lines with HER2 gene amplification.

Cells were seeded in six-well plates at a density of $2\text{-}4\times10^5$ cells per well the day before transfection. Cells were transfected with 2 μg of HER2-targeted TFO or MIX24 using Oligofectamine (Invitrogen) or Dharmafect-1 (Dharmacon) transfection reagent. Transfection was performed as per manufacturer's instructions. siRNA directed against p53, XPD and non-target controls (ON-Target plus SMARTpool reagents; (Dharmacon) were transfected into BT474 cells using Dharmafect-1 transfection reagent (Dharmacon) according to the manufacturers instructions. Western blot analysis was used to confirm knockdown of protein.

Metaphase Chromosome Spreads. Cells were transfected with 2 μg of TAMRA labeled HER2-205. Twenty-four hours post-transfection, cells were treated for 5 h with Colcemid (0.1 μg/μl). Cells were then collected and washed once with PBS. To the cell pellet a 75 mM KCl solution was added for 20 minutes at 37° C. Cell pellets were then resuspended in Carnoy's fixative solution (75% methanol, 25% acetic acid). Following 10 minutes incubation at room temperature, the cells were pelleted and resuspended in an additional 500 μl of Carnoy's fixative solution (3:1 methanol:acetic acid). Cells were dropped from a height onto glass slides and mounting medium with DAPI (Prolong Gold antifade reagent, Invitrogen) was added to each slide. A FITC labeled satellite probe specific for human chromosome 17 (Cytocell) was used to detect gene-specific triplex formation. Pictures were taken of 50-60 metaphase spreads using an Axiovert 200 microscope (Carl Zeiss Micro Imaging, Inc.).

Western blotting. Whole cell lysates were prepared from floating and adherent cells using RIPA buffer according to standard protocols. Total protein (30-50 μg per sample) was resolved by SDS-PAGE. Proteins were detected by a standard immunoblot protocol using the following primary antibodies: cleaved PARP, cleaved caspase 3, γH2AX, XPD, p53, HER2, pHER2 (Y11221/1222), HER3, pHER3 (Y1289), HER4, pHER4 (Y1284), EGFR, pEGFR (Y1068), Chk1, pChk1(S345), pChk2 (T68), and Chk2 (Cell Signaling Technology); pH2AX (tyrosine 142; EMD Millipore); tubulin (clone B-512; Sigma), and GAPDH-HRP (Proteintech). Each experiment was repeated with independent sample preparation a minimum of three times, and representative western blots are shown.

Apoptosis analysis. Cells ($2\text{–}4\times10^5$) were seeded in six-well plates 24 h prior to treatment with MIX24, HER2-1 or HER2-205 (2 μg). Post-treatment analysis was performed using the Annexin V-FITC/PI apoptosis detection kit (BD Pharmingen) according to the manufacturers protocol. Apoptotic frequency was calculated as the combined percentage of early and late apoptotic cells. Data analysis was performed using Flow-Jo software.

Immunofluorescence. Cells were seeded onto UV-irradiated coverslips and were treated for 24 h with HER2-205, MIX24, or a mock transfection. Cells were processed 24 h post-transfection, fixed with 4% formaldehyde and then incubated with ice-cold 100% methanol for 20 minutes followed by a methanol and acetone solution (1:1) for 20 minutes each at −20° C. After washing with PBS, cells were blocked with blocking buffer (4% BSA, 0.2% Triton X-100 in PBS) for 30 minutes and then incubated overnight with the following primary antibodies: γH2AX (1:500; Cell Signaling or Millipore) and 53BP1 (1:100; Santa Cruz) in blocking buffer at 4° C. After three washes, cells were incubated with secondary antibodies Alexa 488 F(ab')2 fragment goat anti-rabbit IgG or Alexa 568 F(ab')2 fragment goat anti-mouse IgG (1:1000; Molecular Probes) for 1 h at room temperature. Cells were then mounted on microscope glass slides with anti-fade mounting media containing DAPI (Life Technologies), and pictures were taken with a Leica SP5 microscope. Immunofluorescence experiments were repeated for validation.

Comet Assay. Neutral comet assays were performed 24 h post TFO-transfection as per the manufacturers instructions (Trevigen) with the adjustment of $3.5\times10^5$ cells/ml for each single cell suspension and 30 minutes electrophoresis. Comets were visualized using an Axiovert 200 microscope and analyzed with Autocomet software. Approximately 100-200 comets were analyzed per experiment. Results were expressed as mean tail moment.

Mouse Models. All mice were maintained at Yale School of Medicine in accordance with guidelines of the Animal Care and Use Committee of Yale University and conformed to the recommendations in the Guide for the Care and Use of Laboratory Animals (Institute of Laboratory Animal Resources, National Research Council, National Academy of Sciences).

Six to seven-week old female BALB/c athymic, ovariectomized nude mice (Harlan Sprague-Dawley) were implanted with 0.72 mg, 60-day release 17β-estradiol pellets (Innovative Research). The following day $2.5\times10^7$ BT474 cells suspended in 100 μl equal volume of media and Matrigel Basement Membrane Matrix (BD Bioscience) were injected subcutaneously in the right flank of each mouse. Mice bearing a tumor of about 100 $mm^3$ in volume were randomly divided into four treatment groups: vehicle (PBS); mixed-sequence oligonucleotide, MIX24; HER2-targeted TFO, HER2-205; and trastuzumab (HERCEPTIN®). Mice were treated with 20 mg/kg body weight of MIX24, HER2-205 or trastuzumab in PBS by intraperitoneal (IP) injection (3 doses evenly administered over 7 days). Tumor volumes in each group were then monitored and mice were sacrificed when tumor volumes reached 1000 $mm^3$. Error bars represent standard error of the mean. Tumor tripling time was calculated as the time required for tumors to increase in volume free-fold over baseline (defined as tumor volume before administration of dose on first day of treatment). Harvested tumors were fixed in 10% neutral buffered formalin and processed by Yale Pathology Tissue Services for H&E, Caspase 3, HER2, and Ki67. Images were taken at 4× magnification.

To establish an ovarian cancer model, female BALB/c athymic nude mice were injected subcutaneously in the flank with $5\times10^6$ SKOV3 cells suspended in 100 μl equal volume of media and Matrigel. Mice bearing a tumor of about 100 $mm^3$ in volume were randomly divided into three treatment groups: vehicle (PBS), n=5; HER2-targeted TFO, HER2-205, n=5; and cisplatin, n=7. HER2-205 (20 mg/kg) and cisplatin (10 mg/kg) were administered by intraperitoneal injection (3 doses/once per week for three weeks). Tumor volumes were monitored and tumor tripling times were calculated as described above.

Gene Expression. RNA was extracted from snap-frozen cells using the RNeasy Kit (Qiagen) per the manufacturers protocol. cDNA synthesis was carried out with 10 μg of RNA via reverse transcription reactions and the High-Capacity cDNA Reverse Transcription Kit (ThermoFisher Scientific). cDNA (10 ng) was then combined with TaqMan Universal PCR master mix (20 μl) (Applied Biosystem) and primers specific to HER2 (HER2, Hs01001580_m1, ThermoFisher Scientific) or the internal control, β-actin (Hs99999903_m1, ThermoFisher Scientific). qRT-PCR was performed in 96-well optical plates in triplicate for each sample. Briefly, reactions were performed at 50° C. for 2 minutes, followed by 95° C. for 10 minutes. Amplification of the target or control gene was carried out with 40 cycles of the two-step reaction, which included 95° C. for 15 seconds and 1 minute at 60° C. β-actin expression levels were used to normalize the difference between cDNA levels in different samples. Relative expression levels were calculated using the 2(-Delta Delta C(T)) method.

Flow Cytometry. BT474 cells were collected 24 h following treatment with either MIX24 HER2-205. After washing with PBS, cells were incubated with 1% paraformaldehyde for 15 minutes on ice. Cells were then fixed with cold 70% ethanol at −20° C. for 2 h or kept for up to 2 weeks until further analysis. Cells were centrifuged and rinsed with PBS, blocked with PBST buffer (1% w/v bovine serum albumin and 0.2% v/v Triton X-100 in PBS) for 15 minutes on ice, followed by another PBS rinse. Cells were first incubated with anti-phospho-ATM (S1981, EMD Millipore) in PBST at 1:100 dilution for 1 h at room temperature. Cells were rinsed with PBST and incubated with anti-rabbit IgG Fab2 Alexa 488 (Molecular Probes) at 1:100 dilution at room temperature for 1 h, and then rinsed with PBST. Acquisition of labeled cells and analysis of data was completed using a flow cytometer (FACS Calibur) and FlowJo software respectively.

Survival Assay. Cell survival seas assayed by visualization of monolayer growth. Briefly, cells were plated at a defined density in 6 or 12-well dishes and treated with either transfection reagent alone (mock), MIX24, or HER2-205 as previously described. Monolayers were visualized by staining cells with crystal violet 72 h post-treatment.

Fluorescence in situ Hybridization (FISH). HER2 and chromosome 17 probes were obtained from Cytocell. The HER2 gene (17q12) probe was labeled with fluorescent Texas Red spectrum and the CEP17 (17p11.1-q11.1) probe was tagged with FITC. PEO1 and SKOV3 cells were treated with colcemid (0.1 μg/ml) for three hours and collected by trypsinizing the monolayer. After washing the cells with PBS, cells were treated with a hypotonic solution (0.075M KCl) at 37° C. for 20 minutes. Cells were then washed and fixed with Carnoy's fixative solution (methanol and acetic acid in 3:1 ratio). Cells were dropped on slides and fluorescent in situ hybridization was performed on the spreads as per the manufacturers instructions. Images were obtained using a Zeiss microscope with Metafer software. A minimum of 50 cells were scored to quantify HER2 and chromosome 17 positive foci.

Statistical analysis. Statistical analysis was performed by one-way or two-way ANOVA with the Tukeys test as post hoc. All analysis was completed using GraphPad Prism software. Herein, ** denotes $p<0.0001$, * denotes $p<0.001$, ** denotes $p<0.01$, and * denotes $p<0.05$.

Results (A) Targeting Gene Amplification in Cancer Via Triplex Formation

Figure 1E:
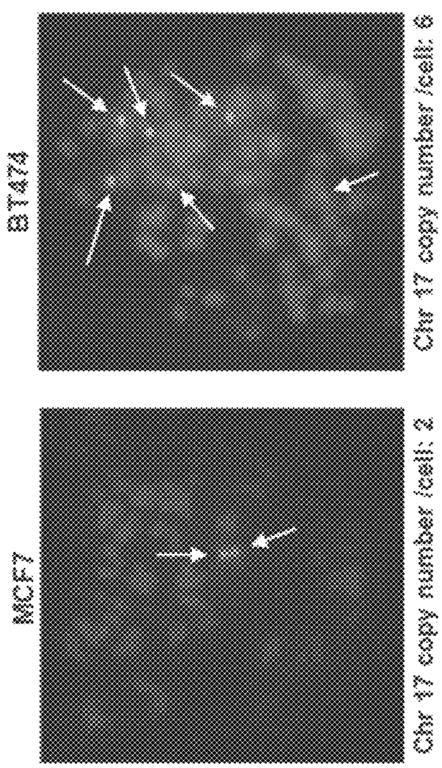

The present disclosure relates to a promising drug platform that directly converts the amplified oncogenic driver genes into DNA damage to trigger cell death (FIG. 1A). This approach employs TFOs that recognize unique polypurine sites within the amplified chromosomal region. First, a TFO, HER2-1, was designed to target the polypurine sequence in the promoter region of the HER2 gene at positions −218 to −245 relative to the transcription start site (FIG. 1I)). Another polypurine site favorable for high affinity triplex formation is located within the coding region beginning at position 205 and was targeted by another TFO, HER2-205 (FIG. ID). Chromosomal TFO binding was confirmed by preparing non-denatured metaphase spreads from MCF7 and BT474 breast cancer cells that had been treated with TAMRA-labeled HER2-205. The generation of chromosomal HER2-205 foci represent third strand binding to fixed chromosomes with intact DNA double helix[15]. Gene-specific triplex formation was verified using a FITC labeled satellite probe specific for human chromosome 17 (FIG. 1E), TAMRA-HER2-205 chromosomal foci were only generated on chromosome 17, the location of the HER2 gene, thus validating target site specificity (FIG. 1E).

Figure 2A:
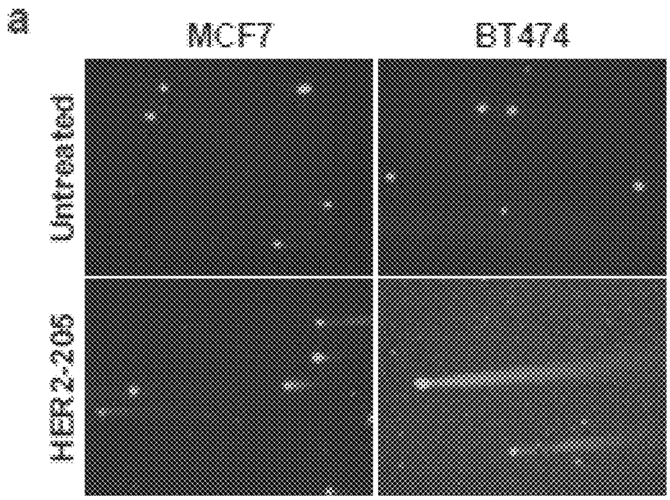
FIGS. 2A-2H include diagrams showing that triplex induced DNA damage and apoptosis correlate with gene copy number. "UT"=untreated cells. "Mock"=cells with transfection reagent only. "MIX24"=cells treated with control mixed sequence oligonucleotide, MIX24. "HER2-1"=HER2-1-treated cells. "HER2-205"=HER2-205-treated cells.
Figure 2B:
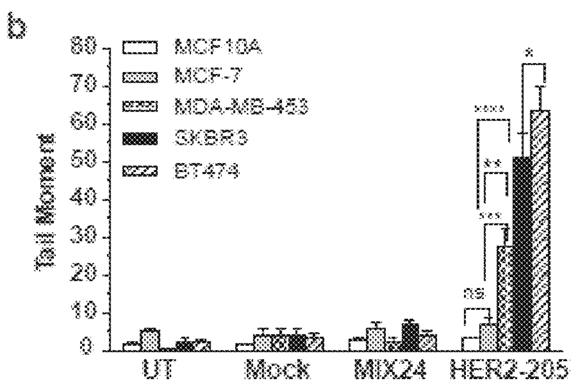
Figure 2C:
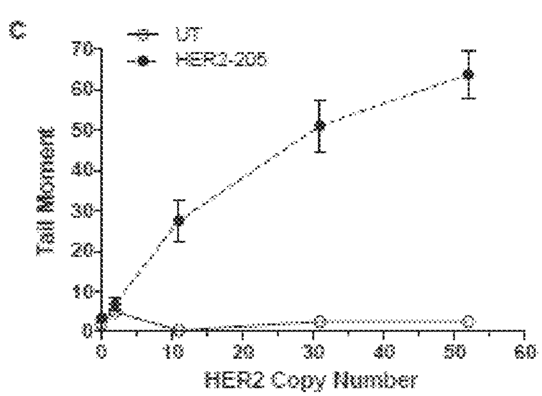
Figure 2D:
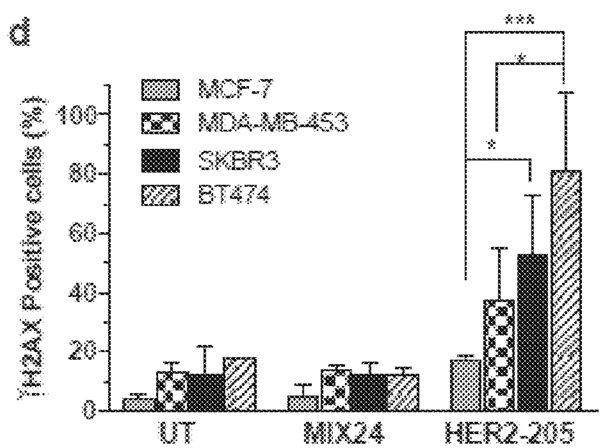
Figure 2E:
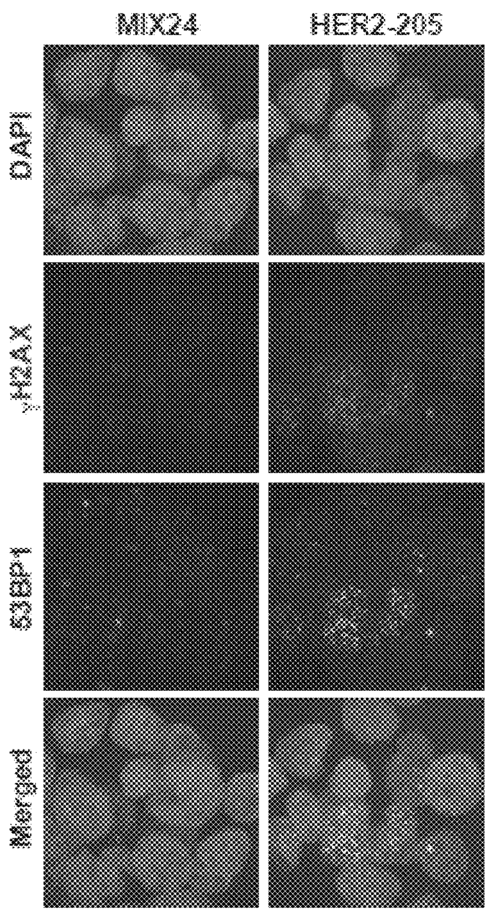
Figure 3A:
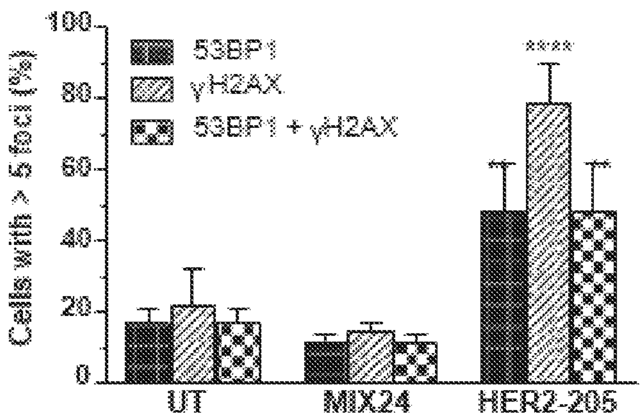
FIG. 3A: a chart showing the quantification of cells with more than 5 γH2AX and/or 53BP1 foci per nuclei in BT474 cells treated with HER2-205 or MIX24.
Figure 3B:
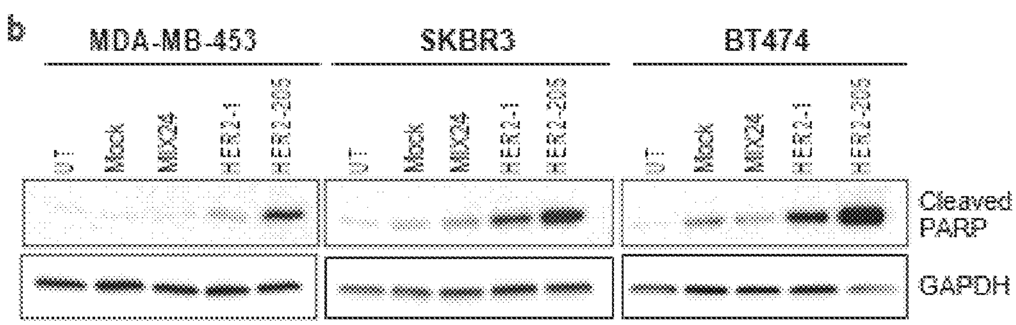
FIG. 3B: images showing that triplex formation induces apoptosis in HER2-positive breast cancer cell lines as measured by Western blot analysis of cleaved PARP.

(B) The Level of Triplex-Induced DNA Damage Correlates with Higher Gene Copy Numbers A neutral comet assay showed that HER2-205 induced significantly more DSBs in cell lines containing multiple copies of the HER2 gene as indicated by an increase in DNA tail moment (FIGS. 2A-2B). Importantly, the level of triplex-induced DNA damage was directly proportional to gene copy number (FIG. 2C). There was also a markedly increased number of γH2AX positive cells, indicative of DSBs, upon treatment of breast cancer cells with high HER2 gene copy numbers (FIG. 2D). Then 53BP1 foci, which colocalize with γH2AX at damage sites, were further assessed. HER2-205 treated BT474 cells exhibited substantially increased γH2AX and 53BP1 foci compared to cells treated with the control oligonucleotide MIX24 (FIG. 2E). Furthermore, colocalization of γH2AX and 53BP1 was observed in 49% of cells following HER2-205 treatment (FIG. 3A).

Figure 2F:
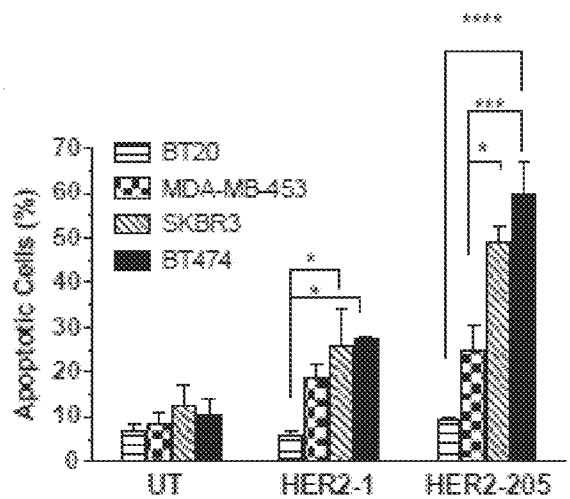
Figure 2G:
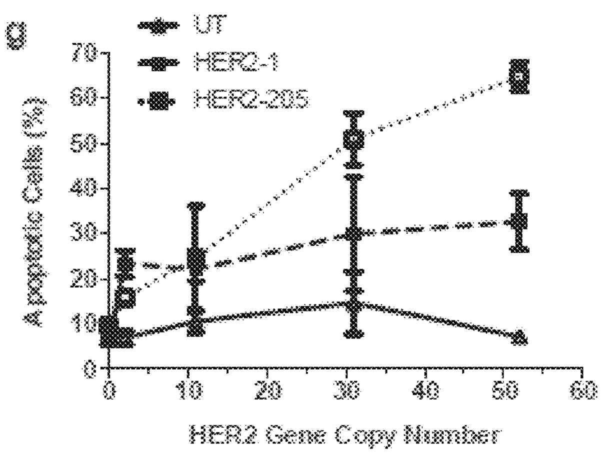

An experiment was conducted to determine whether HER2-targeting TFOs would be capable of inducing apoptosis specifically in amplified breast cancer cells. The results revealed TFO-induced apoptosis specifically in the HER2-positive cell lines and that HER2-205 treatment resulted in a higher percentage of apoptotic cells than that with HER2-1 (FIGS. 2F-2G and FIG. 39). Together, the results demonstrate that the intensity of triplex-induced DNA damage and apoptosis is dependent on gene copy number (FIGS. 2C and 2G). Furthermore, these findings indicate that triplex-induced apoptosis provides the basis to develop novel therapeutics that specifically target amplified cancers, while sparing normal non-amplified tissues.

(C) HER2-205 Treatment Effectively Targets HER2-Positive Ovarian Cancers

Figure 2H:
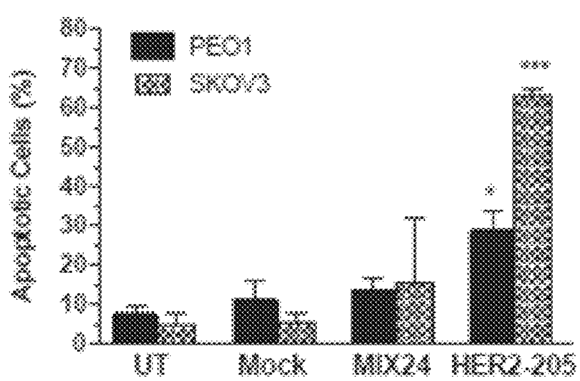
Figure 3C:
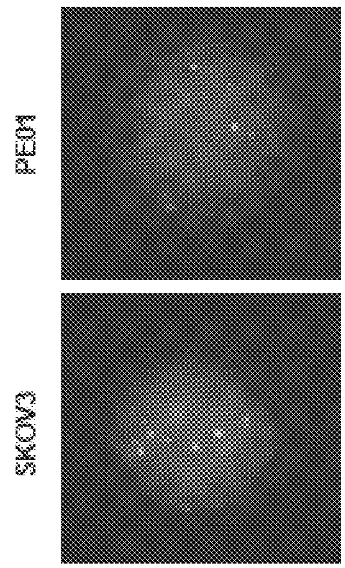
FIG. 3C: images showing the detection of HER2 copies in interphase nuclei by dual color FISH with HER2 probe (red) and chromosome 17 probe (green).
Figure 3D:
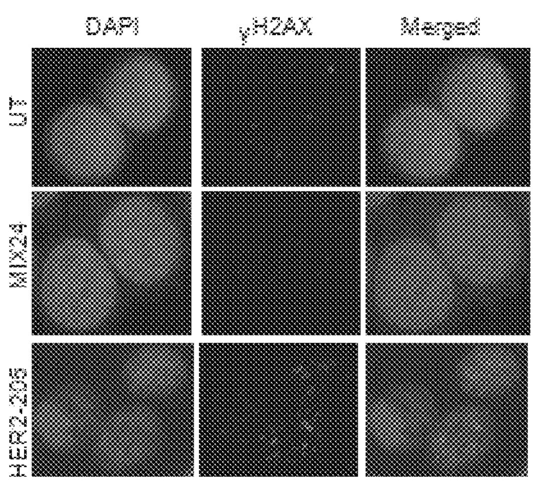
FIG. 3D: images showing the immunofluorescence of γH2AX in PE01 ovarian cancer cells 24 h post-treatment with HER2-205 or MIX24.
Figure 3E:
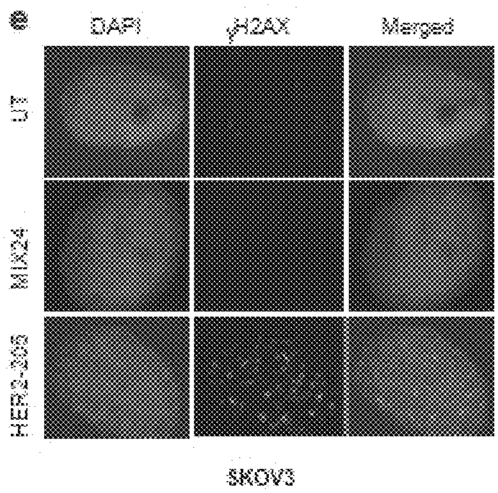
FIG. 3E: representative immunofluorescence images of H2AX foci in SKOV3 ovarian cancer cells 24 h following treatment with HER2-205 or MIX24.
Figure 3F:
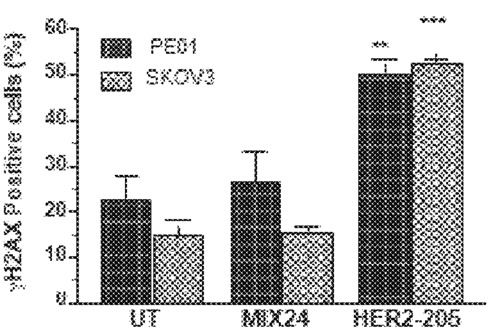
FIG. 3F: a chart showing the frequency of PE01 and SKOV3 cells positive for γH2AX following 24 h treatment.
Figure 3G:
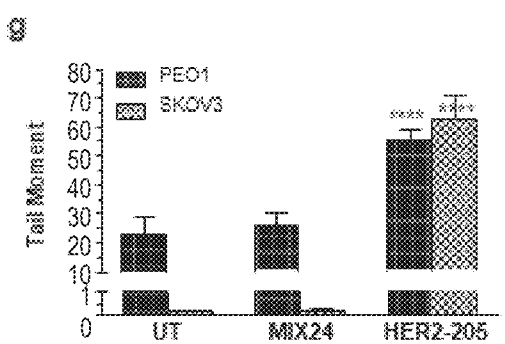
FIG. 3G: a chart showing the quantification of triplex-induced DNA double strand breaks using the neutral comet assay as measured by tail moment.
Figure 3H:
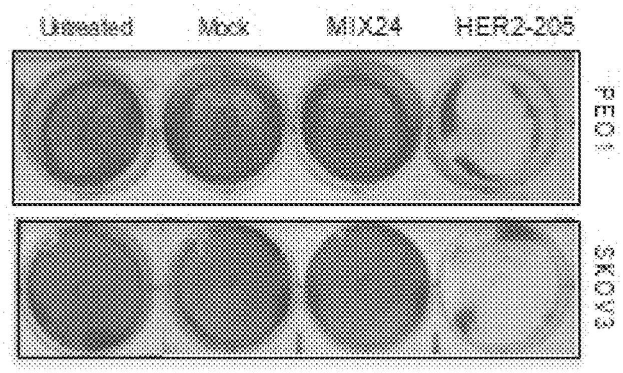
FIG. 3H: images showing is monolayer growth assay that demonstrates a decrease in cell survival in PE01 and SKOV3 cells treated with HER2-205 72 h after treatment.
Figure 3I:
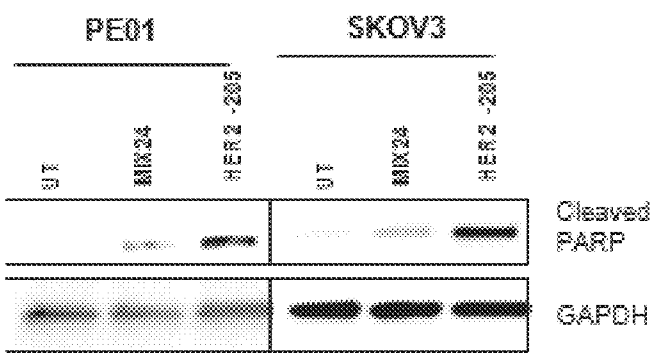
FIG. 3I: images showing a western blot analysis of activation of apoptosis as measured by cleaved PARP ovarian cancer cells following TFO treatment.

The therapeutic efficacy in HER2-positive ovarian cancers was evaluate. When administered to PE01 and SKOV3 cells, both of which have HER2 copy number gains (FIG. 3C), HER2-205 treatment induced increased γH2AX foci and DNA tail moments (FIGS. 3D-G). There were also elevated levels of unrepaired DSBs in the untreated PE01 cells, which harbor a deficiency in BRCA2, a key factor involved in DSB repair by homologous recombination (FIGS. 3F and 3G). Importantly, TFO treatment significantly increased the level of DSBs above baseline (FIG. 3G). In addition, HER2-205 reduced cell viability (FIG. 3H) and activated apoptosis in both cancer cell lines (FIGS. 2H and 3I).

Figure 4A:
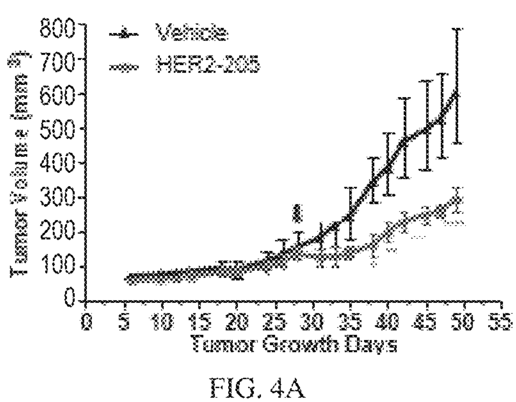
FIGS. 4A-4G include diagrams showing the in vivo effect of HER2-205 on human HER2-positive cancer xenografts. Tumor growth delay curves of BT474 xenografts generated by subcutaneous injection of female athymic nude mice. Twenty-eight days after implantation mice were treated by intraperitoneal (IP) injection with three doses of (FIG. 4A) HER2-205, (FIG. 4B) trastuzumab and (FIG. 4C) MIX24 at a concentration of 20 mg/kg. Arrow indicates administration of first dose. Tumor growth measurements±SEM are shown.
Figure 4B:
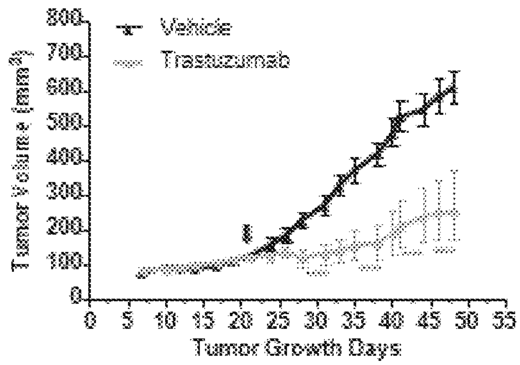
Figure 4C:
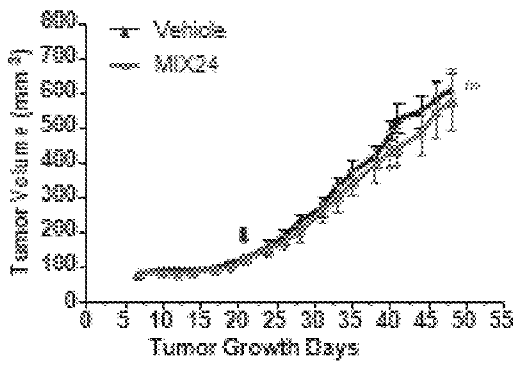
Figure 4D:
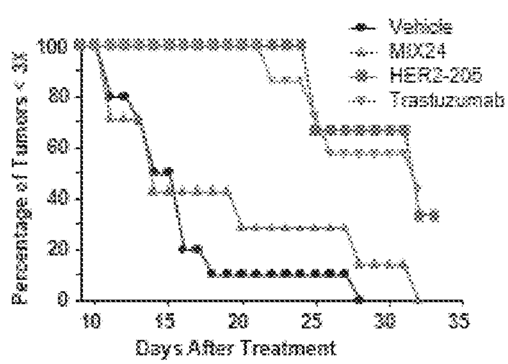
Figure 4E:
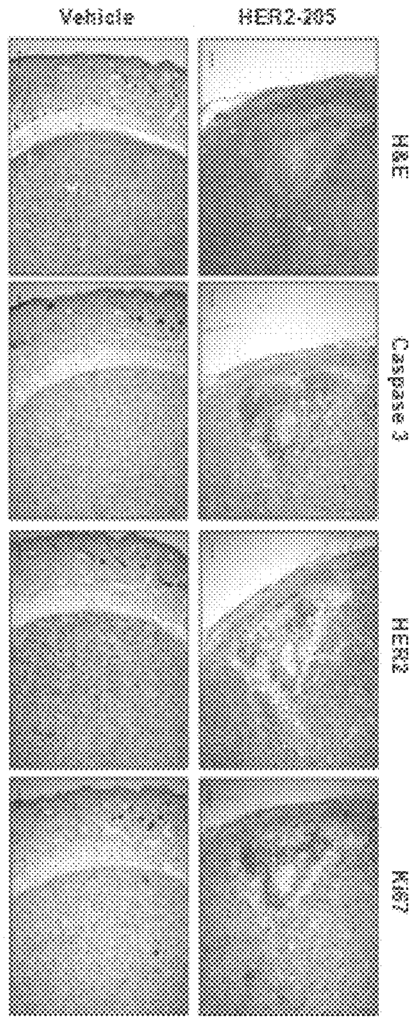
Figure 4F:
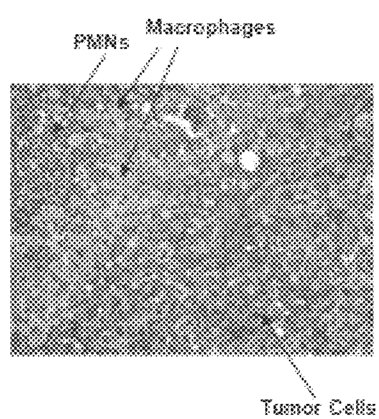

(D) Active HER2-Targeted TFO could Potentially be Used Clinically to Treat HER2-Positive Cancers To test whether active HER2-targeted TFO could be used clinically to treat HER2-positive cancers in a preclinical model, two independent subcutaneous xenograft tumor models were developed. Treatment of BT474 human breast cancer tumors in athymic nude mice with HER2-205 suppressed tumor growth to a significantly greater degree than the controls, vehicle, and MIX24 (FIGS. 4A and 4C). IP administration of HER2-205 resulted in a notable reduction in tumor growth that was comparable to the currently used targeted therapy trastuzumab, thus demonstrating the potential utility of this gene-targeted cancer therapy (FIGS. 4A-4B). A tumor tripling time of 29±5.7 days post-initial dose was observed in tumors treated with HER2-205 compared to 24±2.1 days in tumors treated with trastuzumab (FIG. 4D). In contrast, the control oligonucleotide, MIX24 had no impact on BT474 tumor growth relative to the control buffer alone, with a tumor tripling time for control tumors of 15.7±4.9 days versus 16.3±6.6 days in tumors treated with MIX24 (ANOVA, p=0.99; FIG. 4D). Histological and immunohistochemical analyses were performed on paraffin-embedded tumor tissue sections. Tumor cell apoptosis (evidenced by the presence of cleaved caspase 3), decreased proliferation as measured by Ki67 staining, and a confluent area of tumor necrosis were observed in the HER2-205 treated specimen (FIG. 4E). Magnification of the HER2-205 treated tumor revealed that areas of tumor cell apoptosis are accompanied by a brisk infiltrate of inflammatory cells consisting predominantly of neutrophils and macrophages (FIG. 4F).

Figure 4G:
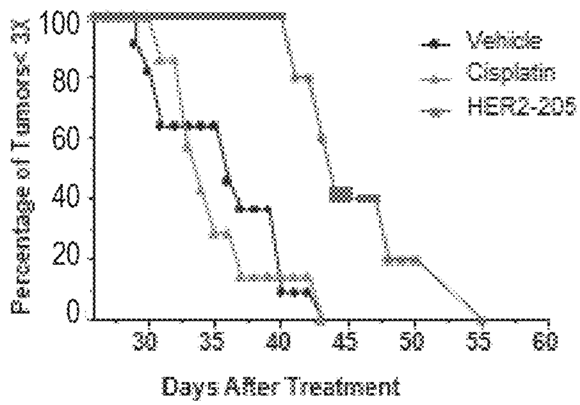

The standard of care for epithelial ovarian cancers consists of platinum-based chemotherapy and surgical cytoreduction[20]. However, as in the case of the SKOV3 cell line, many human ovarian cancers are resistant to platinum-based drugs. Using SKOV3 ovarian cancer xenografts, we find that HER2-205 treatment showed a substantial survival advantage compared with cisplatin (FIG. 4G). HER2-205 demonstrated significant tumor growth inhibitory activity with the average tumor volume being 49% smaller than those in cisplatin-treated mice (ANOVA, p=0.006). These data demonstrate that triplex-induced apoptosis may provide a feasible therapeutic alternative for drug resistant cancers with copy number gains.

Figure 5A:
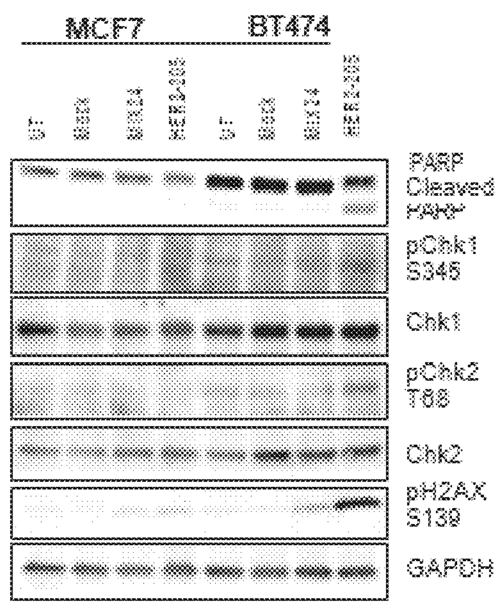
FIGS. 5A-5F include diagrams showing the molecular mechanism of anticancer activity. "UT"=untreated cells. "Mock"=cells with transfection reagent only. "MIX24"=cells treated with control mixed sequence oligonucleotide, MIX24. "HER2-205"=HER2-205-treated cells.
Figure 6A:
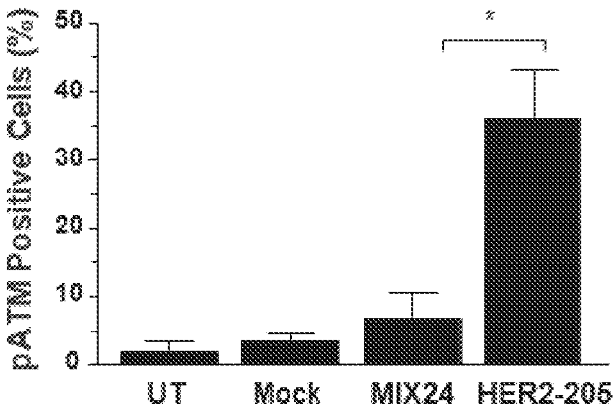
FIGS. 6A-6D include diagrams that support a molecular mechanism that is independent of HER2 signaling pathways. "UT"=untreated cells. "Mock"=cells with transfection reagent only. "MIX24"=cells treated with control mixed sequence oligonucleotide, MIX24. "HER2-205"=HER2-205-treated cells.

(E) Apoptosis Corresponds with the Phosphorylation of Specific DNA Damage Response Proteins and XPD is Required for the Induction of Apoptosis Given that the novelty of the approach herein is based upon the development of agents with a unique mechanism of action, the status of DNA damage response proteins, including ATM, Chk1/Chk2, and the NER factor, XPD in HER2 positive cells was determined following HER2-205 treatment. As shown in FIG. 5A, Chk1 phosphorylation at serine 345 was observed after HER2-205 treatment in the HER2-amplified cells and not in the cells with normal HER2 gene copy numbers. Chk1 activation in BT474 cells corresponds to induction of DSBs and apoptosis as determined by Western blot analysis of pH2AX 5139 and cleaved PARP, respectively. In addition, phosphorylation of Chk2 at threonine 68 was observed in response to triplex-induced DSBs in the BT474 cells (FIG. 5A). These phosphorylation events correspond to an increase in pATM positive cells following HER2-205 treatment (FIG. 6A).

(F) HER2-205 Treatment Activates p53-Independent Apoptosis

Figure 5B:
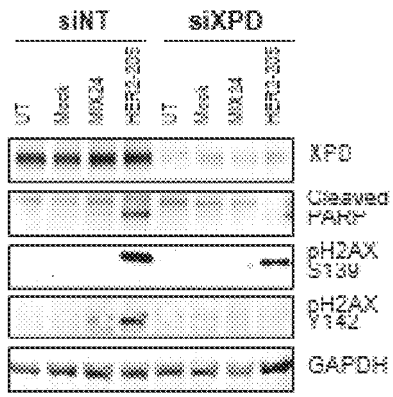
Figure 5C:
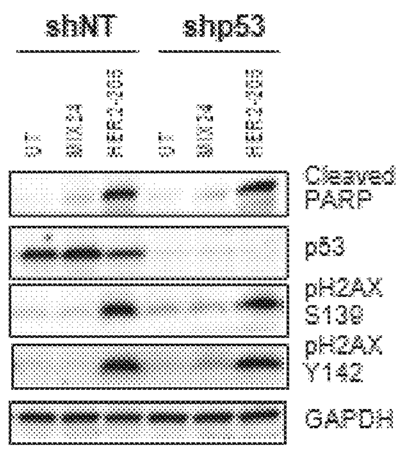

To test whether triplex-induced DNA damage could activate p53-independent apoptosis, p53-depleted BT474 cells were treated with HER2-205. The results showed that TFO-treatment of p53-depleted cells results in a similar level of PARP cleavage compared to treatment of control cells, confirming that triplex formation can activate apoptosis irrespective of p53 status (FIG. 5C). Unlike XPD-depleted cells, which displayed a decrease in TFO-induced apoptosis we also demonstrate that triplex-induced DSBs trigger robust H2AX Y142 phosphorylation in the absence of p53 (FIG. 5C).

Regulation of the phosphorylation status of H2AX at tyrosine 142 (Y142) is crucial for determining the recruitment of either DNA repair or pro-apoptotic factors to the DSBs site[21]. H2AX Y142 was found to phosphorylate in response to HER2-205 induced DSBs to trigger apoptosis as indicated by Western blot analysis of cleaved PARP (FIG. 58). XPD occupies a central role in the mechanism that modulates survival/death decisions in response to triplex-induced DNA damage[15]. Accordingly, a requirement for XPD in the phosphorylation of Y142 in H2AX and activation of apoptosis following HER2-205 treatment was seen (FIG. 5B). These results suggest that the absence of XPD disrupts the signaling pathway used to activate apoptosis following TFO treatment and support a mechanism of action that is dependent upon DNA damage response.

Figure 5D:
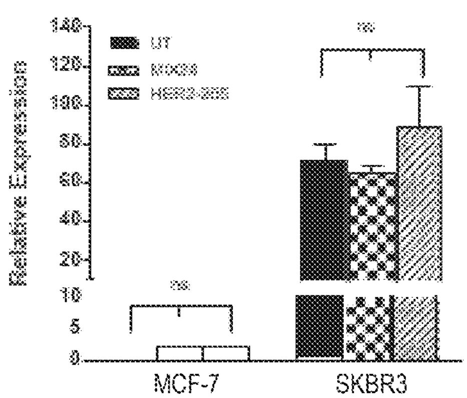
Figure 5E:
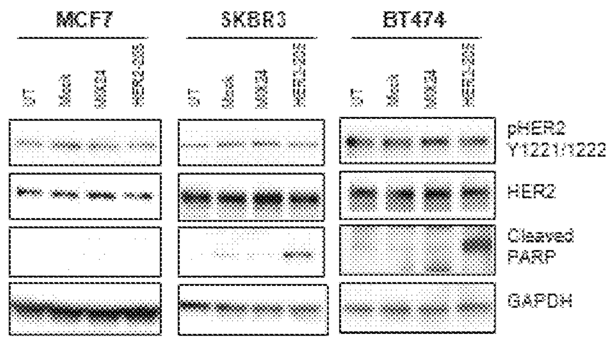
Figure 5F:
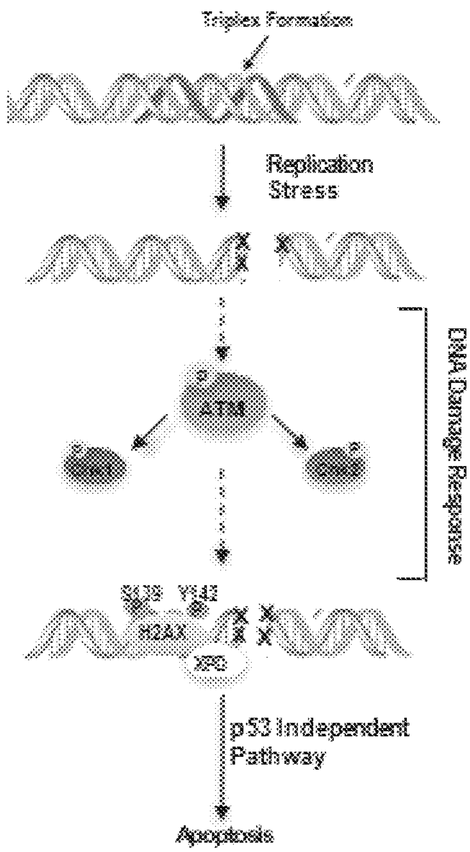
Figure 6B:
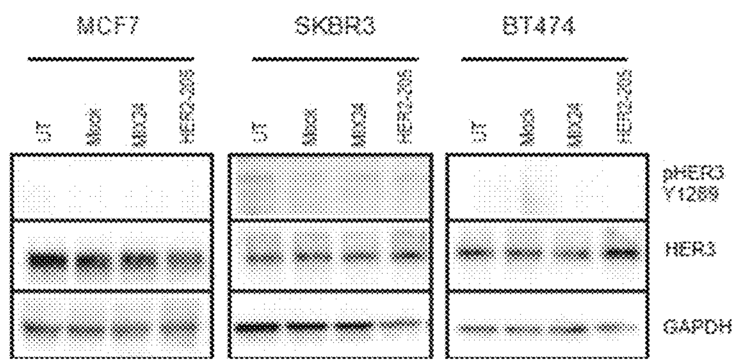
Figure 6C:
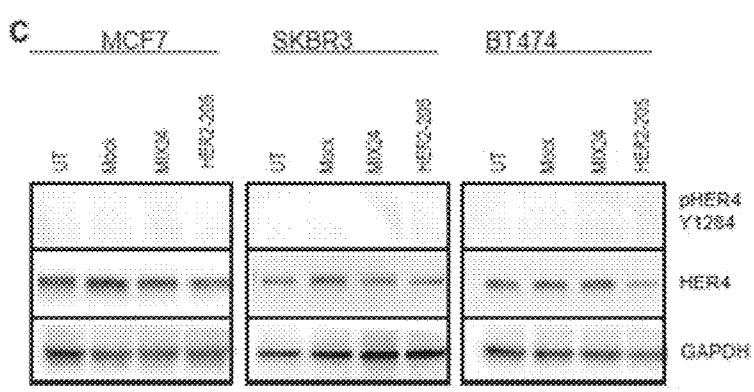
Figure 6D:
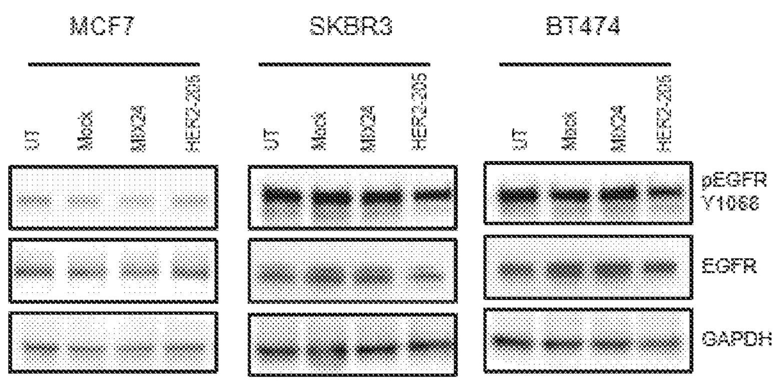

(G) HER2-Targeted TFO Treatment is Independent of HER 2 Gene Expression and Cellular Function Trastuzumab's anticancer activity has been attributed in part to changes in HER2 tyrosine phosphorylation and downregulation of total HER[22,23]. To further demonstrate that HER2-205 activity is based on a mechanism independent of the receptors cellular function, HER2 gene expression was analyzed by RT-PCR (FIG. 5D) and total HER2 protein and phosphorylation levels were monitored by Western blot following treatment in several breast cancer cell lines (FIG. 5E). The results showed that HER2 gene expression is not significantly affected by HER2-205 treatment in either the non-amplified or amplified breast cancer cell lines (FIG. 5D) and that total and activated HER2 levels remain the same following triplex-induced apoptosis in the HER2-positive cells compared to the control samples (FIG. SE). In general, no changes were noted in the levels of HER3, HER4 and EGFR following drug treatment compared to the untreated or MIX24 treated cells (FIGS. 6B-6D). When combined, these studies revealed no consistent evidence of an alteration of the expression or phosphorylation of HER2 or the HER2 family receptors due to drug treatment, thus supporting a mechanism of action that is independent of HER2 cellular function and dependent on DNA damage response (FIG. 5F).

Figure 8A:
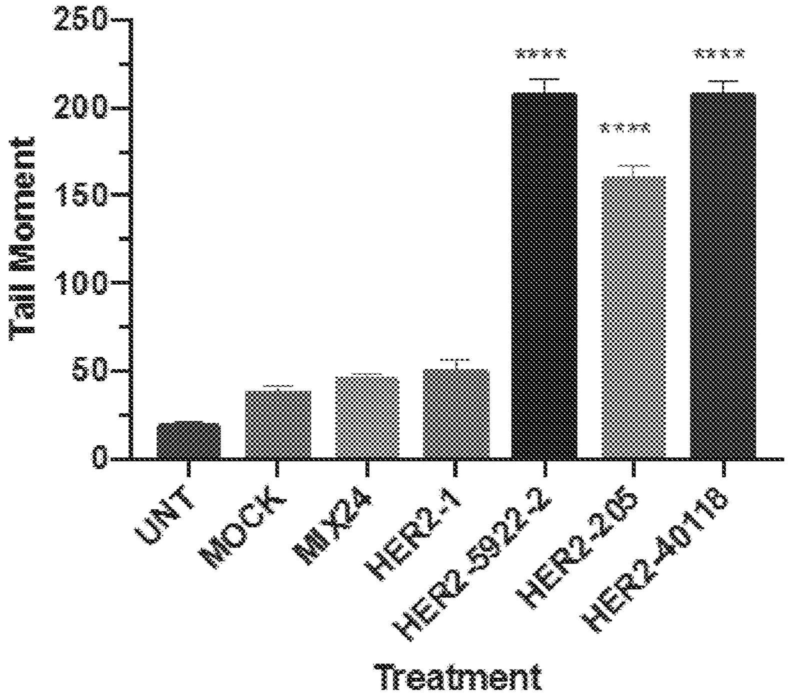
FIGS. 8A-8B include charts showing that TFOs targeting non-coding regions can also induce DSBs and apoptosis.

(H) TFOs Designed to Target Non-Coding Regions of HER2 Gene Induce DNA Double Strand Breaks A neutral comet assay was conducted on BT474 cells 24 hours post-treatment and showed that the TFOs targeting the non-coding regions of HER2 (HER2-5922-2 and HER2-40118) and the TFO targeting the coding region of HER2 (HER2-205) induced significantly, more DSBs in cell lines containing multiple copies of the HER2 gene as indicated by an increase in DNA tail moment (FIG. 8A).

Figure 8B:
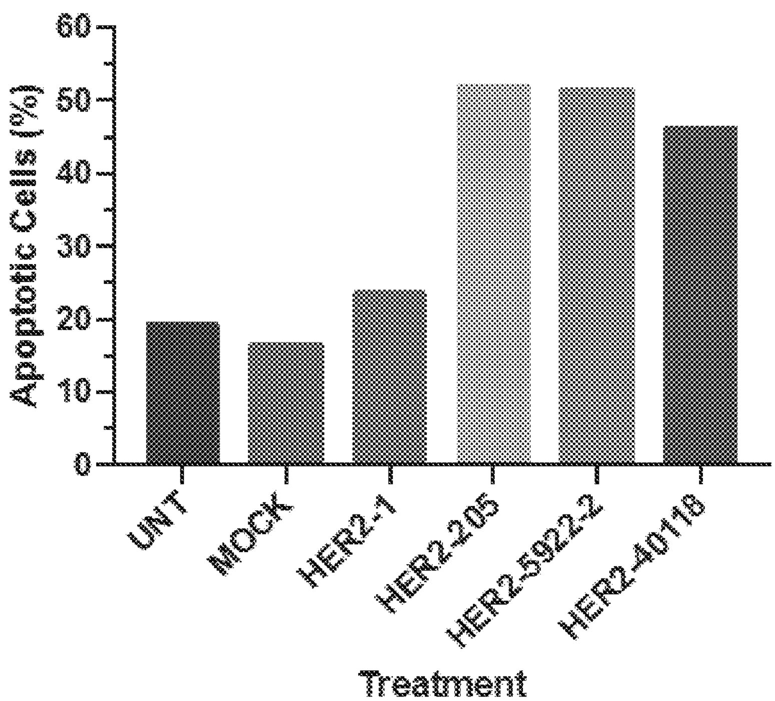

(I) TFOs Designed to Target Non-Coding Regions of the HER2 Gene Activate Apoptosis Triplex-induced apoptosis of BT474 cells was measured by Annexin-V staining. Cells were stained 24 hours post-treatment and the results revealed that TFOs targeting non-coding regions of the HER2 gene can induce. HER2-40118 and HER2-5922-2 TFOs had more than 2-fold the percentage of apoptotic cells 24 hours post-treatment (FIG. 8B).

Discussion

Herein, HER2-205 treatment of HER2-positive breast cancer xenografts resulted in a 52% reduction in tumor volumes compared to controls, which is comparable to the 58% reduction observed with a current HER2-associated chemotherapeutic drug, trastuzumab. TFOs targeting the coding and non-coding regions can induce DNA double strand breaks and apoptosis. Notably, it was confirmed that triplex formation can activate p53-independent apoptosis, which is especially important since p53 mutations are associated with therapeutically challenging cancers. The compositions and methods disclosed herein can be used as drug design platform and treatment option for several cancers with gene amplification and resistance to currently used targeted-therapies.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

REFERENCES

1 Mc, C. B. Chromosome organization and genic expression. *Cold Spring Harb Symp Quant Biol* 16, 13-47 (1951).

2 Matsui, A., Ihara, T., Suda, H., Mikami, H. & Semba, K. Gene amplification: mechanisms and involvement in cancer. *Biomol Concepts* 4, 567-582, doi:10.151.5/bmc-2013-0026 (2013).
3 Santarius, T., Shipley, J., Brewer, D., Stratton, M. R. & Cooper, C. S. A census of amplified and overexpressed human cancer genes. *Nat Rev Cancer* 10, 59-64, doi: 10.1038/nrc2771 (2010).
4 Albertson, D. G. Gene amplification in cancer. *Trends Genet* 22, 447-455, doi:10.1016/j.tig.2006.06.007 (2006).
5 Moasser, M. M. & Krop, I. E. The Evolving Landscape of HER2 Targeting in Breast Cancer. *JAMA Oncol* 1, 1154-1161, doi:10.1.001/jamaoncol.2015.2286 (2015).
6 Swain, S. M. et al. Pertuzumab, trastuzumab, and docetaxel in HER2-positive metastatic breast cancer. *The New England journal of medicine* 372, 724-734, doi: 10.1056/NEJMoa1413513 (2015).
7 Wilks, S, T. Potential of overcoming resistance to HER2-targeted therapies through the PI3K/Akt/mTOR pathway. *Breast* 24, 548-555, doi:10.1016/j.breast.2015.06.002 (2015).
8 Chen, Y. et al. Identification of (huggable cancer driver genes amplified across TCGA datasets. *PloS one* 9, e98: 293, doi:10.1371/journal.pone.0098293 (2014).
9 Ohshima, K. et al. Integrated analysis of gene expression and copy number identified potential cancer driver genes with amplification-dependent overexpression in 1,454 solid tumors. *Sci Rep* 7, 641, doi:10.1038/s41598-017-00219-3 (2017).
10 Slamon, D. J. et al. Studies of the HER-2/neu proto-oncogene in human breast and ovarian cancer. *Science* (New York, N.Y. 244, 707-712 (1989).
11 Baselga, J., Albanell, J., Molina, M. A. & Arribas, J. Mechanism of action of trastuzumab and scientific update. *Seminars in oncology* 28, 4-11 (2001).
12 Petty, R. D. et al. Gefitinib and EGFR Gene Copy Number Aberrations in Esophageal Cancer. *J Olin Oncol* 35, 2279-2287, doi:10.1200/JCO.2016.70.3934 (2017).
13 Pao, W. et al. Acquired resistance of lung adenocarcinomas to gefitinib or erlotinib is associated with a second mutation in the EGFR kinase domain. *PLoS Med* 2, e73, doi:10.1371/journal.pmed.0020073 (2005).
14 Kaushik Ewan, M., Adaku, N., Peart, N. & Rogers, F. A. Triplex structures induce DNA double strand breaks via replication fork collapse in NER deficient cells. *Nucleic acids research* 44, 7742-7754, doi.:10.1093/nar/gkw515 (2016).
15 Kaushik Tiwari, M. & Rogers, F. A. XPD-dependent activation of apoptosis in response to triplex-induced DNA damage. *Nucleic acids research* 41, 8979-8994, doi:10.1093/nar/gkt670 (2013).
16 Rogers, F. A., Vasquez, K. M., Egholm, M. & Glazer, P. M. Site-directed recombination via bifunctional PNA-DNA conjugates. *Proceedings of the National Academy of Sciences of the United States of America* 99, 16695-16700 (2002).
17 Wang, G., Seidman, M. M. & Glazer, P. M. Mutagenesis in mammalian cells induced by triple helix formation and transcription-coupled repair. *Science* (New York, N.Y. 271, 802-805 (1996).
18 Szollosi, J., Balazs, M., Feuerstein, B. G., Benz, C. C. & Waldman, F. M. ERBB-2 (HER2/neu) gene copy number, p185HER-2 overexpression, and intratumor heterogeneity in human breast cancer. *Cancer research* 55, 5400-5407 (1995).
19 Gaddis, S, S. et al. A web-based search engine for triplex-forming oligonucleotide target sequences. *Oligonucleotides* 16, 196-201 (2006).
20 Vergote, I. et al. Neoadjuvant chemotherapy or primary surgery in stage IIIC or IV ovarian cancer. *The New England journal of medicine* 363, 943-953, doi:10.1056/NEJMoa0908806 (2010).
21 Cook, P. J. et al. Tyrosine dephosphorylation of H2AX modulates apoptosis and survival decisions. *Nature* 458, 591-596, doi:10.1038/nature07849 (2009).
22 zum Buschenfelde, C. M., Hermann, C., Schmidt, B., Peschel, C. & Bernhard, H. Antihuman epidermal growth factor receptor 2 (HER2) monoclonal antibody trastuzumab enhances cytolytic activity of class I-restricted HER2-specific T lymphocytes against HER2-overexpressing tumor cells. *Cancer research* 62, 2244-2247 (2002).
23 Cuello, M. et al. Down-regulation of the erbB-2 receptor by trastuzumab (herceptin) enhances tumor necrosis factor-related apoptosis-inducing ligand-mediated apoptosis in breast and ovarian cancer cell lines that overexpress erbB-2. *Cancer Research* 61, 4892-4900 (2001).

What is claimed is:

1. A method of inducing DNA damage in cancer cells, the method comprising contacting the cancer cells with a first triplex forming oligonucleotide (TFO) and a second TFO, wherein:

(a) the cancer cells comprise an amplified HER2 gene that comprises a first polypurine target site and a second polypurine target site that is different from the first polypurine target site, (b) the first TFO is complementary to and hybridizes to the first polypurine target site in the amplified HER2 gene, and the second TFO is complementary to and hybridizes to the second polypurine target site in the amplified HER2 gene, and (c) hybridization of the first TFO to the first polypurine target site and the second TFO to the second polypurine target site in the amplified HER2 gene induces DNA damage in the cancer cells.

2. The method of claim 1, wherein the cancer cells are mammalian cancer cells.

3. The method of claim 1, wherein the cancer cells are human cells.

4. The method of claim 1, wherein each of the first and the second TFO has a length of 13 nucleotides to 30 nucleotides.

5. The method of claim 4, wherein each of the first and second TFO is in a delivery vehicle or is conjugated to a delivery vehicle.

6. The method of claim 5, wherein the delivery vehicle is a nanoparticle.

7. The method of claim 1, wherein each of the first and second TFO has backbone modifications.

8. The method of claim 7, wherein the backbone modifications include phosphorothioates, phosphorodithioates, methylphosphonates, phosphoramidates, boranophosphate oligos, polyamides, methylene(methylimino) linkages, morpholino oligos, or some combination thereof.

9. The method of claim 1, wherein the cancer cells are renal cell carcinoma cells, lung cancer cells, colon cancer cells, colon carcinoma cells, ovarian cancer cells, breast cancer cells, colorectal cancer cells, gastric cancer cells, endometrial cancer cells, brain cancer cells, cells of sarcoma of soft tissue or bone, bone cancer cells, adrenal tumor cells, leukemia cells, pancreatic cancer cells, bladder cancer cells, or hepatocellular carcinoma cells.

* * * * *